(12) United States Patent
Pei

(10) Patent No.: US 7,304,171 B2
(45) Date of Patent: Dec. 4, 2007

(54) COMPOUNDS AND METHODS FOR CYTOPROTECTION

(75) Inventor: Yazhong Pei, San Diego, CA (US)

(73) Assignee: Migenix Corp., San Diego, CA (US)

( * ) Notice: Subject to any disclaimer, the term of this patent is extended or adjusted under 35 U.S.C. 154(b) by 194 days.

(21) Appl. No.: 11/138,105

(22) Filed: May 26, 2005

(65) Prior Publication Data

US 2005/0267086 A1    Dec. 1, 2005

Related U.S. Application Data

(60) Provisional application No. 60/575,162, filed on May 27, 2004.

(51) Int. Cl.
    *C07J 41/00* (2006.01)
(52) U.S. Cl. .................. 552/518; 552/519
(58) Field of Classification Search ............. 552/518, 552/519
    See application file for complete search history.

(56) References Cited

U.S. PATENT DOCUMENTS

| | | | |
|---|---|---|---|
| 4,897,389 A | 1/1990 | Aroonsakul | 514/171 |
| 5,486,511 A * | 1/1996 | Weintraub et al. | 514/178 |
| 5,512,557 A | 4/1996 | Collins | 514/182 |
| 5,521,168 A | 5/1996 | Clark | 514/178 |
| 5,554,601 A | 9/1996 | Simpkins et al. | 514/182 |
| 5,554,603 A | 9/1996 | Kim et al. | 514/182 |
| 5,723,455 A * | 3/1998 | Tanabe et al. | 514/169 |
| 5,824,672 A | 10/1998 | Simpkins et al. | 514/182 |
| 5,843,934 A | 12/1998 | Simpkins | 514/182 |
| 5,859,001 A | 1/1999 | Simpkins et al. | 514/182 |
| 5,866,561 A | 2/1999 | Ungs | 514/182 |
| 5,877,169 A | 3/1999 | Simpkins | 514/179 |
| 5,939,407 A | 8/1999 | Landfield | 514/167 |
| 5,972,923 A | 10/1999 | Simpkins et al. | 514/182 |
| 5,990,078 A | 11/1999 | Toran-Allerand | 514/2 |
| 5,990,177 A | 11/1999 | Brown | 514/729 |
| 6,036,973 A | 3/2000 | Guittard et al. | 424/457 |
| 6,089,941 A | 7/2000 | Glickman et al. | 446/111 |
| 6,140,067 A | 10/2000 | Anderson et al. | 435/26 |
| 6,172,056 B1 | 1/2001 | Droescher et al. | 514/182 |
| 6,172,088 B1 | 1/2001 | Simpkins et al. | 514/340 |
| 6,197,833 B1 | 3/2001 | Simpkins et al. | 514/730 |
| 6,207,658 B1 | 3/2001 | Simpkins et al. | 514/182 |
| 6,232,326 B1 | 5/2001 | Nelson | 514/336 |
| 6,251,863 B1 | 6/2001 | Yue | 514/12 |
| 6,258,856 B1 | 7/2001 | Chamberlain et al. | 514/912 |
| 6,274,603 B1 | 8/2001 | Poirier | 514/330 |
| 6,319,914 B1 | 11/2001 | Simpkins et al. | 514/182 |
| 6,326,365 B1 | 12/2001 | Simpkins et al. | 514/179 |
| 6,333,317 B1 | 12/2001 | Lee et al. | 514/162 |
| 6,334,998 B1 | 1/2002 | Uckun et al. | 424/9.1 |
| 6,339,078 B1 | 1/2002 | Simpkins et al. | 514/179 |
| 6,350,739 B1 | 2/2002 | Simpkins et al. | 514/182 |
| 6,420,353 B1 | 7/2002 | Lathe et al. | 514/182 |
| 6,432,643 B1 | 8/2002 | Einstein et al. | 435/6 |
| 6,511,969 B1 | 1/2003 | Hermsmeyer | 514/177 |
| 6,566,064 B1 | 5/2003 | Shiraki et al. | 435/6 |
| 6,605,605 B2 | 8/2003 | Hammerly | 514/178 |
| 6,677,324 B1 | 1/2004 | Knauthe et al. | 514/170 |
| 6,692,763 B1 | 2/2004 | Cummings et al. | 424/449 |
| 6,844,456 B2 | 1/2005 | Covey | 552/545 |
| 6,958,327 B1 * | 10/2005 | Hillisch et al. | 514/182 |
| 2001/0051602 A1 | 12/2001 | Poirier | 514/2 |
| 2002/0022593 A1 | 2/2002 | Yue | 514/12 |
| 2002/0028793 A1 | 3/2002 | Wassermann | 514/171 |
| 2002/0035100 A1 | 3/2002 | Prokai et al. | 514/182 |
| 2002/0102725 A1 | 8/2002 | Zabarovsky et al. | 435/325 |
| 2002/0132802 A1 | 9/2002 | Covey | 514/178 |
| 2002/0165213 A1 | 11/2002 | Weiss et al. | 514/182 |
| 2002/0183299 A1 | 12/2002 | Voskuhl | 514/182 |
| 2003/0045510 A1 | 3/2003 | Schloss et al. | 514/171 |

(Continued)

FOREIGN PATENT DOCUMENTS

EP    0 753 300 A1    1/1997

(Continued)

OTHER PUBLICATIONS

Peters et al., J. Med. Chem., vol. 32, No. 7, pp. 1642-1652, 1989.*

(Continued)

Primary Examiner—Barbara P. Badio
(74) Attorney, Agent, or Firm—Seed IP Law Group PLLC

(57) ABSTRACT

Compounds, compositions and methods for treating degenerative diseases and disorders are disclosed, the compounds having the following structure (I):

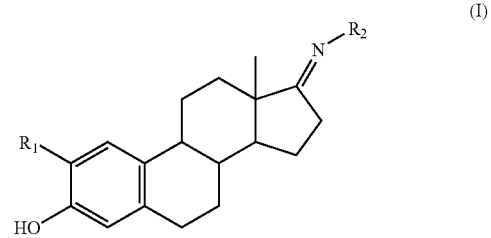

including stereoisomers, prodrugs and pharmaceutically acceptable salts thereof, wherein $R_1$ and $R_2$ are as defined herein.

11 Claims, No Drawings

U.S. PATENT DOCUMENTS

| | | | |
|---|---|---|---|
| 2003/0049838 A1 | 3/2003 | Thompson et al. | 435/368 |
| 2003/0050295 A1 | 3/2003 | Pang | 514/182 |
| 2003/0119796 A1 | 6/2003 | Strony | 514/170 |
| 2003/0129134 A1 | 7/2003 | Chenard et al. | 424/9.3 |
| 2003/0130303 A1 | 7/2003 | Coe et al. | 514/300 |
| 2003/0176409 A1 | 9/2003 | Offner | 514/182 |
| 2003/0186954 A1 | 10/2003 | Hermsmeyer | 514/182 |
| 2004/0043410 A1 | 3/2004 | Carnazza | 435/6 |
| 2004/0067923 A1 | 4/2004 | Elger et al. | 514/182 |
| 2004/0223963 A1 | 11/2004 | Cheung et al. | 424/94.65 |
| 2004/0259886 A1 | 12/2004 | Day et al. | 514/256 |
| 2005/0031651 A1 | 2/2005 | Gervais et al. | 424/400 |

FOREIGN PATENT DOCUMENTS

| | | |
|---|---|---|
| WO | WO 01/10430 A2 | 2/2001 |
| WO | WO 02/13870 A2 | 2/2002 |
| WO | WO 02/36605 A2 | 5/2002 |
| WO | WO 03/015704 A2 | 2/2003 |
| WO | WO 03/072109 A1 | 9/2003 |
| WO | WO 03/072110 A1 | 9/2003 |

OTHER PUBLICATIONS

Chemical Abstract Service, Accession No. 1992:235946, 1992.
El-Khawass, S., et al., "Steroidal Derivatives. Part 2. Synthesis and Endocrinologic Properties of Novel Acylhydrazone Derivatives of Steroids," Pharmazie, 35(3):143-145, 1980.
Liu, R., et al., "Neuroprotective Effects of a Novel Non-receptor-binding Estrogen Analogue: In Vitro and in Vivo Analysis," Stroke, 33(10):2485-91, Oct. 2002.
Peters, R., et al., "17-Desoxy Estrogen Analogues," J Med Chem., 32(7):1642-52, Jul. 1989.
Xia, S., et al., "The Estrogen Receptor is Not Essential for All Estrogen Neuroprotection: New Evidence from a New Analog," Neurobiol Dis., 9(3):282-93, Apr. 2002.
Badeau, M., et al., "Estrogen A-ring Structure and Antioxidative Effect on Lipoproteins," J Steroid Biochem Mol Biol., 96(3-4):271-8, Aug. 2005.
Behl, C., et al., "17-beta Estradiol Protects Neurons from Oxidative Stress-induced Cell Death in Vitro," Biochem Biophys Res Commun., 216(2):473-82, Nov. 13, 1995.
Behl, C., et al., "Neuroprotection Against Oxidative Stress by Estrogens: Structure-activity Relationship," Mol Pharmacol., 51(4):535-41, Apr. 1997.
Betts, J., et al., Neuropathological Aspects of Mitochondrial DNA Disease, Neurochem Res., 29(3):505-11, Mar. 2004.
Buzdar, A., TAS-108: A Novel Steroidal Antiestrogen, Clin Cancer Res., 11(2 Pt 2):906s-8s, Jan. 15, 2005.
Conrad, K., et al., "Emerging Role of Relaxin in Renal and Cardiovascular Function," Am J Physiol Regul Integr Comp Physiol., 287(2):R250-61, Aug. 2004.
Deshpande, S., "Protective Role of Estrogen in the Neurodegenerative Disorder," Indian J Physiol Pharmacol., 44(1):43-9, Jan. 2000.
Doggrell, S., "Experimental and Clinical Studies Show That the Probucol Derivative AGI-1067 Prevents Vascular Growth," Expert Opin Investig Drugs., 12(11):1855-9, Nov. 2003.
Du, D-M., et al Development of bivalent acetylcholinesterase inhibitors as potential therapeutic drugs for Alzheimer's disease, Curr Pharm Des., 10(25):3141-56, 2004.
Dykens, J., et al., "Polycyclic Phenols, Estrogens and Neuroprotection: A Proposed Mitochondrial Mechanism," Exp Gerontol., 38(1-2):101-7, Jan.-Feb. 2003.
Eng-Wong, J., et al., "Raloxifene and Its Role in Breast Cancer Prevention," Expert Rev Anticancer Ther., 4(4):523-32, Aug. 2004.
Finsterer, J., "Mitochondriopathies," Eur J Neurol., 11(3):163-86, Mar. 2004.
Garcia-Segura, L., et al., "Neuroprotection by estradiol," Prog Neurobiol., 63(1):29-60, Jan. 2001.
Gradishar, W., "Tamoxifen—what Next?," Oncologist, 9(4):378-84, 2004.
Hayes, E., "Biology of Primate Relaxin: A Paracrine Signal in Early Pregnancy," Reprod Biol Endocrinol., 2:36, Jun. 16, 2004.
Kompoliti, K., "Estrogen and Parkinson's Disease," Front Biosci., 8:s391-400, May 1, 2003.
Kulkarni, J., et al., "A Clinical Trial of Adjunctive Oestrogen Treatment in Women with Schizophrenia," Arch Women Ment Health., 5(3):99-104, Nov. 2002.
Kupina, N., et al., "Cytoskeletal Protein Degradation and Neurodegeneration Evolves Differently in Males and Females Following Experimental Head Injury," Exp Neurol., 180(1):55-73, Mar. 2003.
Leibelt, D., et al., "Evaluation of Chronic Dietary Exposure to Indole-3-carbinol and Absorption-enhanced 3,3'-diindolylmethane in Sprague-dawley Rats," Toxicol Sci., 74(1):10-21, Jul. 2003.
Lord, R., et al., "Estrogen Metabolism and the Diet-cancer Connection: Rationale for Assessing the Ratio of Urinary Hydroxylated Estrogen Metabolites," Altern Med Rev. 7(2):112-29, Apr. 2002.
McCullough, L., et al., "Estrogen and Ischemic Neuroprotection: An Integrated View," Trends Endocrinol Metab., 14(5):228-35, Jul. 2003.
McDonnell, D., "The Molecular Pharmacology of Estrogen Receptor Modulators: Implications for the Treatment of Breast Cancer," Clin Cancer Res., 11(2 Pt 2):871s-7s, Jan. 15, 2005.
Montagna, P., et al., "MELAS Syndrome: Characteristic Migrainous and Epileptic Features and Maternal Transmission," Neurology, 38(5):751-4, May 1998.
Mooradian, A., "Antioxidant Properties of Steroids," J Steroid Biochem Mol Biol., 45(6):509-11, Jun. 1993.
Moosmann, B., et al. "The Antioxidant Neuroprotective Effects of Estrogens and Phenolic Compounds are Independent from Their Estrogenic Properties," PNAS, 96:8867-8872, Aug. 1999.
Nikov, G., et al., "Interactions of Synthetic Estrogens with Human Estrogen Receptors," J. Endocrinol., 170:137-145, 2001.
Pavlakis, S., et al., "Mitochondrial Myopathy, Encephalopathy, Lactic Acidosis, and Strokelike Episodes: A Distinctive Clinical Syndrome," Ann Neurol., 16(4):481-8, Oct. 1984.
Rapala, R., et al., "The Adamantly Group in Medicinal Agents. II. Anabolic Steroid 17γ-Adamantoates," J. Med. Chem. 8:580-583, 1965.
Ruszkowska, J., et al., "Tryptophan-derived Sulfur-containing Phytoalexins—A General Overview," Adv Exp Med Biol., 527:629-36, 2003.
Scheffler, Mitochondria, Wiley-Liss, New York, 1999, Ch. 7, "Mitochondrial Mutations and Disease," pp. 273-325.
Simpkins, J., et al., "Mitochondria Play a Central Role in Estrogen-induced Neuroprotection," Curr Drug Targets CNS Neurol Disord., 4(1):69-83, Feb. 2005.
Tardif, J., "Clinical Results with AGI-1067: a Novel Antioxidant Vascular Protectant," Am J Cardiol., 91(3A):41A-49A, Feb. 6, 2003.
Tardif, J., et al., "Pharmacologic Prevention of Both Restenosis and Atherosclerosis Progression: AGI-1067, Probucol, Statins, Folic Acid and Other Therapies," Curr Opin Lipidol., 14(6):615-20, Dec. 2003.
Wang, X., et al., "Oxidative Damage to Human Lens Epithelial Cells in Culture: Estrogen Protection of Mitochondrial Potential, ATP, and Cell Viability," Invest Ophthalmol Vis Sci., 44(5):2067-75, May 2003.
Wasserman, M., et al., "Chemistry and Pharmacology of Vascular Protectants: A Novel Approach to the Treatment of Atherosclerosis and Coronary Artery Disease," Am J Cardiol., 91(3A):34A-40A, Feb. 6, 2003.
Zemlyak, I., et al., "Protection Against gp120-induced Neurotoxicity by An Array of Estrogenic Steroids," Brain Res., 958(2):272-6, Dec. 27, 2002.

* cited by examiner

COMPOUNDS AND METHODS FOR CYTOPROTECTION

CROSS-REFERENCE TO RELATED APPLICATION

This application claims the benefit of U.S. Provisional Patent Application No. 60/575,162, filed May 27, 2004, which is incorporated herein by reference in its entirety.

BACKGROUND OF THE INVENTION

1. Field of the Invention

The present invention relates generally to novel classes of cytoprotective steroid (cyclopentanophenanthrene-related) compounds, as well as to compositions and methods for using such compounds to treat degenerative disorders including degenerative diseases and related conditions, and in particular, disorders associated with undesirable cell death or cell damage.

2. Description of the Related Art

Numerous degenerative diseases, disorders and conditions afflicting humans and animals are characterized by detrimental damage to tissues and cells, often resulting in undesirably compromised cellular activity and frequently leading to cell death. Recent technological refinements provide insights into a detailed molecular understanding of such cytodegeneration, including, inter alia, appreciation of the roles of: genetic and environmental factors; reactive free radicals (e.g., reactive oxygen species); excitotoxic, autoimmune and inflammatory mechanisms; and characterization of cellular death processes such as apoptosis and necrosis. The scope of degenerative diseases, and their costs to society, are extensive, with massive impacts on the basic quality of life and on human productivity.

Degenerative disorders include a large number of acute, relapsing/remitting and/or chronic debilitating conditions that feature cell death or cellular damage, such as neurological and neurodegenerative diseases (e.g., Alzheimer's disease, Huntington's disease, Parkinson's disease, amyotrophic lateral sclerosis, multiple sclerosis, mild cognitive impairment, etc.), circulatory and cardiac disease (e.g., atherosclerosis, diabetes, ischemia, heart failure, etc.), cancer, autoimmune and inflammatory diseases, inherited genetic diseases and disorders, traumatic injuries, arthritis, metabolic and digestive diseases, ophthalmologic diseases or injuries, dermatological, musculoskeletal, endocrine, renal, hepatic, gastrointestinal, and respiratory disorders, and many others.

The estrogen steroid hormones (e.g., 17-β-estradiol, estrone) and structurally related derivative compounds have attracted considerable interest as candidate cytoprotectants for use in the treatment of degenerative disorders, and in particular as neuroprotectants, based on a number of chemical and biological properties (see, e.g., U.S. Pat. Nos. 6,692,763, 6,511,969, 6,420,353, 6,334,998, 6,333,317, 6,258,856, 6,232,326, 6,172,056, 6,089,941, 5,990,177, 5,866,561, 5,521,168, 5,512,557, U.S. 2004/0067923, WO 03/072109, WO 03/072110, U.S. 2004/0043410, U.S. 2003/0186954, U.S. 2003/0176409, U.S. 2003/0130303, U.S. 2003/0050295, U.S. 2003/0049838, U.S. 2002/0183299, U.S. 2002/0165213, U.S. 2002/0028793, U.S. 2002/0022593, U.S. 2001/0051602, WO 03/015704, U.S. Pat. No. 4,897,389, EP 753,300, U.S. Pat. No. 5,554,603; see also Dykens et al., 2003 Exp. Gerontol. 38(1-2):101-107; Wang et al., 2003 Invest. Ophthalmol. Vis. Sci. 44(5):2067-75; Garcia-Segura et al., 2001 Prog. Neurobiol. 63(1):29-60; Deshpande et al., 2000 Ind. J. Physiol. Pharmacol. 44(1) 43-49; Behl et al., 1995 Biochem. Biophys. Res. Commun. 216:473-82; McCullough et al., 2003 Trends Endocrinol. Metab. 14(5):228-235; Kulkami et al., 2002 Arch. Women Ment. Health 5:99-104; Zemlyak et al., 2002 Brain Res. 958:272-76; Kompoliti, 2003 Front. Biosci. 8:391-400; Mooradian, 1993 J. Steroid Biochem. Molec. Biol. 45(6): 509-511; Kupina et al., 2003 Exp. Neurol. 180:55-73).

Despite these efforts, a number of avenues remain unexplored with regard to the relevance of these compounds to particular applications or disease indications, including the relationship of chemical properties to desired biological, physiological and/or pharmacological properties, the relative ease of synthesis (or of isolation in the case of naturally derived estrogen compounds, for which purity and lot-to-lot consistency may also pose challenges), efficacy as cytoprotectants, stability, bioavailability, adaptability to suitable formulations, and other considerations. Recent progress in this area has been described, for example in U.S. Pat. No. 6,844,456, U.S. 2002/0132802, U.S. 2002/0035100, U.S. Pat. Nos. 5,554,601, 5,824,672, 5,843,934, 5,859,001, 5,877,169, 5,939,407, 5,972,923, 6,172,088, 6,197,833, 6,207,658, 6,319,914, 6,326,365, 6,339,078, 6,350,739, WO 01/10430, WO 02/13870, U.S. 2003/0105167. Clearly, however, there remains a need for additional compounds that can be optimized for use as cytoprotectants, including demonstration of the suitability of such compounds for use in the treatment of degenerative disorders and diseases in a physiologically relevant context. The present invention addresses this need by providing compositions and methods for therapeutically beneficial cytoprotection, and offers other related advantages.

BRIEF SUMMARY OF THE INVENTION

In brief, this invention is generally directed to compounds that have activity as cytoprotectants, as well as to methods for their use, and to pharmaceutical compositions containing the same. More specifically, the compounds of this invention have the following general structure (I):

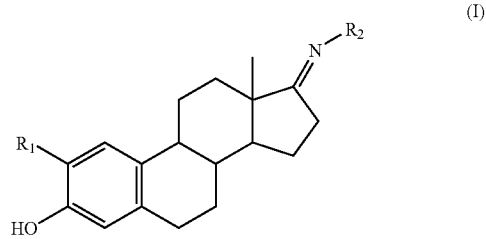

including stereoisomers, prodrugs and pharmaceutically acceptable salts thereof, wherein $R_1$ and $R_2$ are as defined herein.

The compounds of this invention have utility over a wide range of therapeutic applications, and may be used to treat degenerative disorders, degenerative diseases and related conditions, and in particular, disorders associated with undesirable cell death or cell damage. For example, a number of degenerative disorders and diseases are associated according to non-limiting theory with altered activity of an excitotoxic pathway leading to inappropriate cell death via apoptotic or necrotic processes, such that unexpectedly advantageous cytoprotective properties of compounds described herein may be usefully applied in the management of such conditions. Accordingly, certain embodiments relate to a method for treating a degenerative disorder, comprising administering a therapeutically effective amount of a compound of structure (I) to a subject having or suspected of being at risk for having a degenerative disorder. In certain embodiments the degenerative disorder is selected from (i) a neurodegenerative disorder, (ii) an ophthalmic disease, (iii) a cardiovascular disease, (iv) a disorder of bone, joint, connective tissue or cartilage, (v) a disorder associated with altered activity of an excitotoxic pathway, (vi) tissue transplantation and (vi) a mitochondrial disorder (e.g., Friedreich's ataxia). In another embodiment the degenerative disorder is Alzheimer's disease, mild cognitive impairment, Parkinson's disease, amyotrophic lateral sclerosis or multiple sclerosis. In another embodiment the degenerative disorder is an ophthalmic disease that is selected from glaucoma, retinitis pigmentosa, macular degeneration, elevated intraocular pressure and Leber's hereditary optic neuropathy. In another embodiment the degenerative disorder is a cardiovascular disease that is selected from the group consisting of stroke, ischemia and myocardial infarction. In another embodiment the degenerative disorder is a disorder of bone, joint, connective tissue or cartilage that is selected from osteoarthritis, rheumatoid arthritis and psoriatic arthritis.

The methods of this invention include in certain embodiments administering an effective amount of a compound of structure (I) above, preferably in the form of a pharmaceutical composition, to a mammal in need thereof. Thus, in another embodiment, pharmaceutical compositions are disclosed containing one or more compounds of this invention in combination with a pharmaceutically acceptable carrier and/or diluent. In a distinct embodiment the invention provides a pharmaceutical composition comprising (i) a first cytoprotective compound that is a compound of structure (I); (ii) at least one second compound that is selected from an antioxidant, an antiestrogen, a hormone, a mineral, a vitamin, a neuropeptide, a cholesterol-lowering agent, an Alzheimer's disease-treating agent, a stroke-treating agent and a therapeutic antibody; and (iii) a pharmaceutically acceptable carrier. In another embodiment there is provided a method for treating a degenerative disorder, comprising administering, to a subject having or suspected of being at risk for having a degenerative disorder, a therapeutically effective amount of the pharmaceutical composition comprising (i), (ii) and (iii) as just described. In another embodiment there is provided a method for treating a degenerative disorder, comprising administering, to a subject having or suspected of being at risk for having a degenerative disorder, a therapeutically effective amount of (i) a first cytoprotective compound that is a compound of structure (I), and (ii) at least one second compound that is selected from an antioxidant, an antiestrogen, a cruciferous indole compound, probucol or an analog of probucol, relaxin hormone, tacrine, a neurotrophin, a statin, melatonin, a sterol or 5-alpha-stanol absorption inhibitor, calcium and vitamin D. In a further embodiment the first cytoprotective compound and the second compound are administered separately, and in a different further embodiment the first cytoprotective compound and the second compound are administered together.

In another embodiment the invention provides a method for isolating a molecular component of an excitotoxic pathway, comprising contacting a biological sample with a compound of structure (I) or a derivative thereof, under conditions and for a time sufficient to permit a binding interaction between the compound and the molecular component, and thereby isolating the pathway component. In certain further embodiments, the compound is immobilized, detectably labeled or retrievably tagged.

These and other aspects of the present invention will become apparent upon reference to the following detailed description. To this end, various references are set forth herein which describe in more detail certain background information, procedures, compounds and/or compositions, and are each hereby incorporated by reference as if set forth in their entirety.

DETAILED DESCRIPTION OF THE INVENTION

The present invention relates in pertinent part and in certain embodiments to surprising cytoprotective properties of a class of steroid (cyclopentanophenanthrene-related) compounds described in greater detail hereinbelow. As also described herein, these cytoprotective compounds may be used therapeutically to treat degenerative disorders including degenerative diseases by reducing (i.e., decreasing in a statistically significant manner) the level of clinically harmful, deleterious or otherwise detrimental cellular death or damage to cells that may accompany such degenerative conditions. A particularly advantageous feature of cytoprotective (including neuroprotective) compounds disclosed herein is that despite their structural similarities to the estrogen class of steroid hormones, the presently described cytoprotective compounds are substantially nonfeminizing insofar as they do not comprise significant feminizing activity. As such, these nonfeminizing cytoprotective compounds may be administered to male and female patients with minimal risk of feminizing activity, for example, as may be of concern with regard to feminizing effects exhibited by other estrogens and estrogen-like compounds in such tissues as breast, skin and (in females) uterus. Feminizing estrogens also increase prothrombic factors in the liver, which are tied to increased risk of stroke, pulmonary embolism, coronary heart disease and the like. The non-feminizing compounds of the present invention minimize the risk of such disorders when administered to male and female subjects.

As mentioned above, the present invention is thus directed generally to compounds having activity as cytoprotectants, as well as to methods for their use and pharmaceutical compositions containing the same. The compounds of this invention have the following general structure (I):

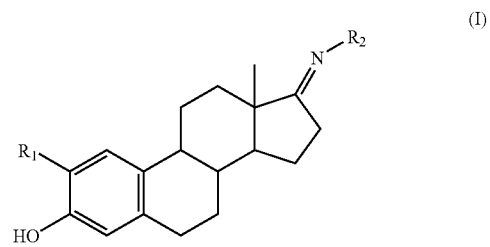

or a stereoisomer, prodrug or pharmaceutically acceptable salt thereof, wherein:

$R_1$ is alkyl, substituted alkyl, aryl, substituted aryl, arylalkyl or substituted arylalkyl;

$R_2$ is $-NR_{3a}R_{3b}$, $-O-R_{3a}$, or $-NR_{3a}C(=O)R_{3b}$; and $R_{3a}$ and $R_{3b}$ are the same or different and independently selected from hydrogen, alkyl, substituted alkyl, aryl, substituted aryl, arylalkyl, substituted arylalkyl, heterocycle and substituted heterocycle.

As used herein, the following terms have the following meanings:

"Alkyl" means a straight chain or branched, saturated or unsaturated, cyclic or non-cyclic hydrocarbon having from 1 to 14 carbon atoms, while "lower alkyl" has the same meaning but only has from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Unsaturated alkyls contain at least one double or triple bond between adjacent carbon atoms (also referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like. Representative saturated cyclic alkyls include cyclopropyl, cyclobutyl, cyclopentyl, cyclohexyl, —CH$_2$cyclohexyl and the like; while unsaturated cyclic alkyls include cyclopentenyl, cyclohexenyl, —CH$_2$cyclohexenyl and the like. Cyclic alkyls are also referred to herein as "carbocyclic" rings systems, and include bi- and tri-cyclic ring systems having from 8 to 14 carbon atoms, such as a cycloalkyl (such as cyclopentane or cyclohexane) fused to one or more aromatic (such as phenyl) or non-aromatic (such as cyclohexane) carbocyclic rings. Representative carbocyclic moieties include adamantyl and the like.

"Halogen" means fluorine, chlorine, bromine or iodine.

"Oxo" means a carbonyl group (i.e., =O).

"Nitro" means —NO$_2$.

"Mono- or di-alkylamino" means an amino substituted with one alkyl or with two alkyls, respectively.

"Alkanediyl" means a divalent alkyl from which two hydrogen atoms are taken from the same, or different, carbon atoms, such as —CH$_2$—, —CH$_2$CH$_2$—, —CH$_2$CH$_2$CH$_2$—, —CH(CH$_3$)CH$_2$—, and the like.

"Aryl" means an aromatic carbocyclic moiety such as phenyl or naphthyl.

"Arylalkyl" means an alkyl having at least one alkyl hydrogen atom replaced with an aryl moiety, such as benzyl, —(CH$_2$)$_2$phenyl, —(CH$_2$)$_3$phenyl, —CH(phenyl)$_2$, and the like.

"Heteroaryl" means an aromatic heterocycle ring of 5 to 10 members and having at least one heteroatom selected from nitrogen, oxygen and sulfur, and containing at least 1 carbon atom, including both mono- and bi-cyclic ring systems. Representative heteroaryls include pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

The term "substituted" as used herein means any of the above groups (e.g., alkyl, aryl, arylalkyl, heteroaryl, heteroarylalkyl, heterocycle and heterocyclealkyl) wherein at least one hydrogen atom is replaced with a substituent. In the case of an oxo substituent ("=O") two hydrogen atoms are replaced. Substituents include halogen, hydroxy, oxo, alkyl, substituted alkyl (such as mono- or di-substituted aminoalkyl, alkyloxyalkyl, and the like), aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, —NR$_c$C(=O)NR$_a$R$_b$, —NR$_a$C(=O)OR$_b$, —NR$_a$SO$_2$R$_b$, —OR$_a$, —C(=O)R$_a$, —C(=O)OR$_a$, —C(=O)NR$_a$R$_b$, —OC(=O)R$_a$, —OC(=O)OR$_a$, —OC(=O)NR$_a$R$_b$, —NR$_a$SO$_2$R$_b$, —CONR$_a$(alkanediyl)OR$_b$, —CONR$_c$(alkanediyl-O)$_{1-6}$(alkanediyl)NR$_a$R$_b$, or a radical of the formula —Y-Z-R$_a$ where Y is alkanediyl, substituted alkanediyl or a direct bond, Z is —O—, —S—, —S(=O)—, —S(=O)$_2$—, —N(R$_b$)—, —C(=O)—, —C(=O)O—, —OC(=O)—, —N(R$_b$)C(=O)—, —C(=O)N(R$_b$)— or a direct bond, wherein R$_a$, R$_b$ and R$_c$ are the same or different and independently hydrogen, amino, alkyl, substituted alkyl (including halogenated alkyl), aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl, or wherein R$_a$ and R$_b$ taken together with the nitrogen atom to which they are attached form a heterocycle or substituted heterocycle.

In describing the location of groups and substituents, the following numbering system will be employed, to conform the numbering of the cyclopentanophenanthrene nucleus to the convention used by the IUPAC and Chemical Abstracts Service.

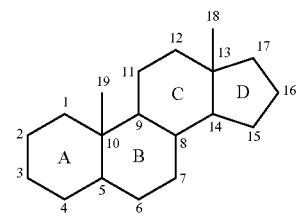

In addition, the term "steroid" as used herein is intended to mean compounds having the aforementioned cyclopentanophenanthrene nucleus.

The compounds of the present invention may generally be utilized as the free acid or free base. Alternatively, the compounds of this invention may be used in the form of acid or base addition salts (e.g., as a sulfated salt, a phosphate, a nitrate, a benzoate, an ascorbate or the like). Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The compounds of structure (I), as well as the more specific embodiments discussed below, may be made by techniques knows to those skilled in the field of organic chemistry, and as more specifically exemplified in the Examples.

In one embodiment, $R_2$ is —$NR_{3a}R_{3b}$ and the compounds have the following structure (II):

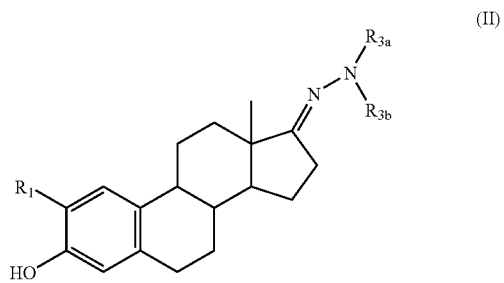

In another embodiment, $R_2$ is —O—$R_{3a}$ and the compounds have the following structure (III):

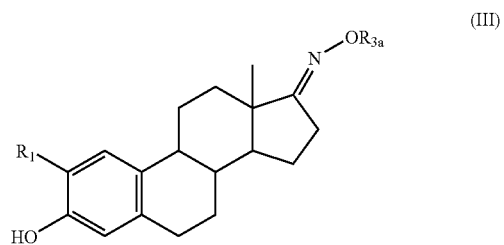

In another embodiment, $R_2$ is —$NR_{3a}C(=O)R_{3b}$ and the compounds have the following structure (IV):

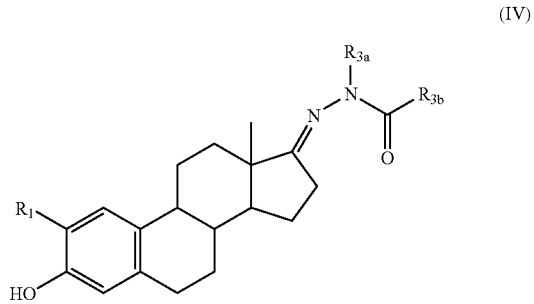

In more specific embodiments of the foregoing structures (II), (III) and (IV), $R_1$ is alkyl. In still more specific embodiment, $R_1$ is adamantyl and the compounds have the following structures (II-1), (III-1) and (IV-1):

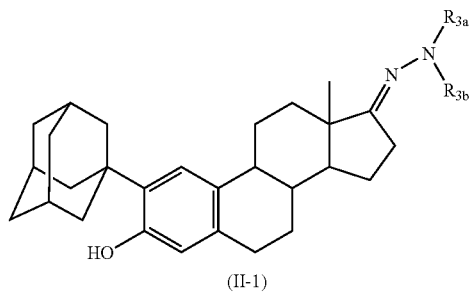

-continued

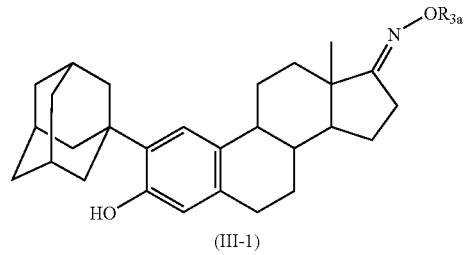

(III-1)

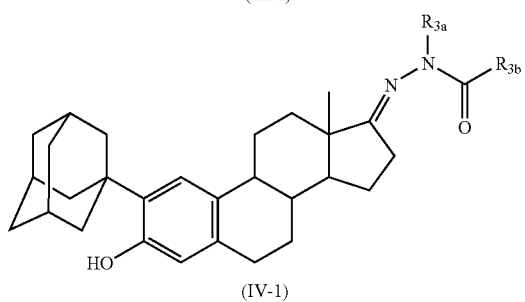

(IV-1)

In more specific embodiments of the foregoing structures (II-1), (III-1) and (IV-1), $R_{3a}$ and $R_{3b}$ are independently selected from hydrogen and lower alkyl.

As mentioned above, the compounds of this invention have utility over a wide range of therapeutic applications, and may be used to treat or prevent a degenerative disorder, which may include any disease, disorder, syndrome or other condition wherein cell degeneration is present, or is expected to be present, in a subject or biological source, and in preferred embodiments where such cell degeneration is a primary or secondary factor in the disorder. Cell degeneration may be manifest as a statistically significant increase in cell death or cytostasis within one or more affected organs, tissues or other anatomical sites, for example, as a localized increase in apoptosis and/or necrosis that may be determined according to art-established methodologies (e.g., Green et al., 1998 *Science* 281:1309). Cell degeneration may also be present in the form of harmful damage to cells, for example as a consequence of exposure to reactive free radicals such as reactive oxygen species (ROS) or other radicals, where biomarkers for such cellular damage have been described (e.g., Halliwell and Gutteridge, *Free Radicals in Biology and Medicine* (3$^{rd}$ Ed.), 1999 Oxford Univ. Press, N.Y.).

As noted above, an increasing number of diseases, disorders and conditions have been identified as degenerative disorders as provided herein, such that given the present disclosure and the state of the art with respect to methods for assessing cellular viability and/or damage, and with respect to clinical signs and symptoms of such disorders, the person having ordinary skill in the art can readily determine criteria for establishing a statistically significant deviation from a normal range for one or more parameters that are appropriate to the definition of the disease, in order to establish that a degenerative disorder is present. See, for instance, *Current Medical Diagnosis and Treatment* 2004—(43$^{rd}$ ed.), L. M. Tierney et al., 2003 McGraw-Hill, N.Y.; *Prognosis of Neurological Disorders*—2d. Ed., W. Randolph et al. (Eds.) 2000 Oxford Univ. Press, N.Y.; *Multiple Sclerosis: Diagnosis, Medical Management and Rehabilitation*, J. S. Burks and K. P. Johnson, 2000 Demos Medical Publishing, N.Y.; and *Parkinson's Disease and Its Diagnosis*, J. M. S. Pearse 1992 Oxford Medical Publications, Oxford Univ. Press, N.Y.

As an illustrative example, where it is desirable to determine whether or not a subject or biological source falls within clinical parameters indicative of multiple sclerosis (MS), signs and symptoms of MS that are accepted by those skilled in the art may be used to so designate a subject or biological source, for example clinical signs referred to in McDonald et al. (2001, *Annals of Neurology* 50(1):121-127) and references cited therein, or other means known in the art for diagnosing MS. Similarly, those familiar with the art will be aware of art accepted criteria for determining the presence of other degenerative disorders as provided herein.

Degenerative disorders for which it is contemplated that one or more cytoprotective compounds disclosed herein will provide therapeutic benefit include chronic, acute and/or remitting/relapsing disorders, and thus also include:

neurodegenerative disorders, for instance, disorders that are characterized by a progressive loss of neurons in the peripheral nervous system and/or in the central nervous system; neurological and neurodegenerative diseases and conditions such as Alzheimer's disease, Parkinson's disease (PD), amyotrophic lateral sclerosis (ALS), multiple sclerosis (MS), peripheral neuropathy, shingles, stroke, traumatic injury, cognitive impairment, mild cognitive impairment, traumatic and other brain injury, Huntington's disease, age-related dementia and memory impairment, peripheral nerve damage, cerebral edema, hematoma; various neurological and other degenerative consequences of neurological and chest surgeries, schizophrenia and epilepsy, Down's Syndrome, Turner's Syndrome, spinal cord injury, hypoglycemia;

degenerative conditions associated with acquired immune deficiency syndrome (AIDS);

alcohol-induced dementia, Wernicke-Korsakoff related dementia;

various disorders of bone, joint, connective tissue and/or cartilage, such as bone disorders including osteoporosis, osteomyclitis, ischemic bone disease, fibrous dysplasia, rickets, Cushing's syndrome and osteoarthritis, other types of arthritis and conditions of bone, joint, connective tissue and/or cartilage degeneration including rheumatoid, psoriatic arthritis; muscle wasting disorders such as muscular dystrophy, Duchenne Muscular Dystrophy, etc.; skin disorders such as dermatitis, eczema, psoriasis and skin aging; impaired wound healing;

disorders of the ear such as otosclerosis;

various cardiovascular diseases such as diseases and conditions of the heart and vasculature, including ischemia of cardiac and other tissues, myocardial infarction, chronic or acute heart failure, cardiac dysrhymias, artrial fibrillation, paroxymial tachycardia, ventricular fibrillation and congestive heart failure, anoxia, hypoxia; also including circulatory disorders including atherosclerosis, arterial sclerosis and peripheral vascular disease, diabetes (Type I or Type II); other cardiovascular diseases including stroke; various diseases of the lung including pneumonia, chronic obstructive lung disease (bronchitis, emphysemia, asthma);

disorders of the gastrointestinal tract such as ulcers and hernia; dental conditions that feature tissue damage such as periodontitis; liver diseases including hepatitis and cirrhosis; pancreatic ailments including acute pancreatitis; kidney diseases such as acute renal failure and glomerulonephritis;

various blood disorders such as vascular amyloidosis, aneurysms, anemia, hemorrhage, sickle cell anemia, autoimmune disease, red blood cell fragmentation syndrome, neutropenia, leukopenia, bone marrow aphasia, pancytopenia, thrombocytopenia, hemophilia; and the like;

ophthalmic diseases, disorders or injuries including diabetic retinopathy, glaucoma, macular degeneration (e.g., atrophic or "dry" macular degeneration, exudative or "wet" macular degeneration, and age-related macular degeneration), retinal degeneration, retinitis pigmentosa (RP), retinal tears or holes, retinal detachment, retinal ischemia, acute retinopathies associated with trauma, inflammatory mediated degeneration, post-surgical complications, damage associated with laser therapy including photodynamic therapy (PDT), surgical light induced iatrogenic retinopathy, drug-induced retinopathies, autosomal dominant optic atrophy, toxic/nutritional amblyopias; Leber's Hereditary Optic Neuropathy (LHON), elevated intraocular pressure, other mitochondrial diseases with ophthalmic manifestations or complications, ocular angiogenesis/neovascularization; anterior ischemic optic neuropathy; Atypical RP; Bardet-Biedl Syndrome; Best Disease; Blue-Cone Monochromacy; Bull's-eye maculopathy; Cataracts; Central Areolar Choroidal Dystrophy; Choroideremia; Cone Dystrophy; Rod Dystrophy; Cone-Rod Dystrophy; Rod-Cone Dystrophy; Congenital Stationary Night Blindness; Cytomegalovirus Retinitis; Diabetic macular edema; Dominant Drusen; Giant Cell Arteritis (GCA); Goldmann-Favre Dystrophy; Graves' Ophthalmopathy; Gyrate Atrophy; chloroquine-induced retinopathy; Iritis; Juvenile Retinoschisis; Kearns-Sayre Syndrome; Laurence-Moon Syndrome; Leber Congenital Amaurosis; Lupus-induced Cotton Wool Spots; Macular Drusen; Macular Dystrophy; Malattia Leventinese; ocular histoplasmosis syndrome; Oguchi Disease; Oxidative damage; Proliferative Vitreoretinopathy; Refsum Disease; Retinitis Punctata Albescens; retinopathy of prematurity; Rod Monochromatism; RP and Usher syndrome; Scleritis; Sector RP; Sjogren-Larsson Syndrome; Sorsby Fundus Dystrophy; Stargardt Disease, and other degenerative disorders of the eye including other retinal diseases;

mitochondrial disorders, including in particular Friedreich's ataxia and also including mitochondrial myopathy-encephalopathy-lactic acidosis-and-stroke (MELAS), progressive external ophthalmoplegia (PEO), diabetes, myoclonus-epilepsy associated with ragged-red fibers (MERRF), mitochondriopathy-associated dementia, epilepsy, ataxia, retinopathy, optic atrophy, renal failure, bone marrow failure, and other diseases associated with mitochondrial dysfunction (see, e.g., Simpkins et al., 2005 *Curr. Drug Targets-CNS & Neurolog. Dis.* 4:69-83; Finsterer, 2004 *Eur. J. Neurol.* 11:163; Betts et al., 2004 *Neurochem Res.* 29:505; Pavlakis et al., 1984 *Ann. Neurol.* 16:481; Montagna et al, 1988 *Neurology* 38:751; Beal, Howell and Bodis-Wollner (Eds.), *Mitochondria and Free Radicals in Neurodegenerative Diseases,* 1997 Wiley-Liss, New York; Scheffler, *Mitochondria,* 1999 Wiley-Liss, New York, Ch. 7 (pp. 273-325)). Without wishing to be bound by theory, cytoprotective compounds disclosed herein may be usefully and beneficially administered under conditions and for a time sufficient to mediate protective, stabilizing and/or anti-oxidative effects on mitochondria, thereby preserving mitochondrial function as it relates to maintenance and perpetuation of a variety of cellular processes, including aerobic respiration and generation of metabolic energy (e.g., ATP production), monitoring and mediating intracellular calcium homeostasis, modulating cell viability through such processes as excitotoxicity, apoptosis and necrosis, and other roles. Thus, and further according to such non-limiting theory, presently disclosed cytoprotective compounds are believed to render mitochondria in cells resistant to various environmental insults and/or genetically based dysfunction which could otherwise predispose the cells to proceed along apoptotic, exitotoxic and/or necrotic pathways that underlie degenerative conditions as described herein.

Accordingly, compounds disclosed herein may have remedial, therapeutic, palliative, rehabilitative, preventative and/or prophylactic effects on patients suffering from, or potentially predisposed to developing, diseases and disorders associated with alterations in mitochondrial function, including degenerative disorders described herein. Such diseases may be characterized by abnormal, supernormal, inefficient, ineffective or deleterious mitochondrial activity, for example, defects in uptake, release, activity, sequestration, transport, metabolism, catabolism, synthesis, storage or processing of biomolecules and/or co-factors involved in mitochondrial function (e.g., ATP, calcium, glycolytic precursors, intermediates or products, electron transport chain and oxidative phosphorylation pathway components including electron donors, acceptors and related intermediates and co-factors, pro- and anti-apoptotic factors, etc.) and/or by inappropriate, harmful or otherwise deleterious directly- or indirectly-mitochondrially interacting biological molecules and macromolecules such as proteins and peptides and their derivatives, carbohydrates and oligosaccharides and their derivatives including glycoconjugates such as glycoproteins and glycolipids, lipids, nucleic acids and cofactors including ions, mediators, precursors, catabolites and the like.

Such diseases and disorders include, by way of example and not limitation, chronic neurodegenerative disorders such as Alzheimer's disease (AD) and Parkinson's disease (PD); auto-immune diseases; diabetes mellitus, including Type I and Type II; mitochondria associated diseases, including but not limited to congenital muscular dystrophy with mitochondrial structural abnormalities, fatal infantile myopathy with severe mtDNA depletion and benign "later-onset" myopathy with moderate reduction in mtDNA, MELAS (mitochondrial encephalopathy, lactic acidosis, and stroke) and MIDD (mitochondrial diabetes and deafness); MERFF (myoclonic epilepsy ragged red fiber syndrome); arthritis; NARP (Neuropathy; Ataxia; Retinitis Pigmentosa); MNGIE (Myopathy and external ophthalmoplegia; Neuropathy; Gastro-Intestinal; Encephalopathy), LHON (Leber's Hereditary Optic Neuropathy), Kearns-Sayre disease; Pearson's Syndrome; PEO (Progressive External Ophthalmoplegia); Wolfram syndrome; DIDMOAD (Diabetes Insipidus, Diabetes Mellitus, Optic Atrophy, Deafness); Leigh's Syndrome; dystonia; schizophrenia; and hyperproliferative disorders, such as cancer, tumors and psoriasis.

Other degenerative disorders for which it is contemplated that one or more cytoprotective compounds disclosed herein will provide therapeutic benefit include ischemic conditions and diseases (see, e.g., U.S. Pat. Nos. 5,877,169 and 6,339,078), and in particular, ischemic disorders affecting neuronal, endothelial and/or cardiac cells. Ischemic events thus include cerebrovascular disease, subarachnoid hemorrhage, myocardial infarct, surgery, trauma, and blockage of blood flow through a vessel.

By way of brief background, ischemia is an acute condition associated with an inadequate flow of oxygenated blood to a part of the body, caused by the constriction or blockage of the blood vessels supplying it. Ischemia occurs any time that blood flow to a tissue is reduced below a critical level. This reduction in blood flow can result from: (i) the blockage of a vessel by an embolus (blood clot); (ii) the blockage of a vessel due to atherosclerosis; (iii) the breakage of a blood vessel (a bleeding stroke); (iv) the blockage of a blood vessel due to vasoconstriction such as occurs during vasospasms and possibly, during transient ischemic attacks (TIA) and following subarachnoid hemorrhage. Conditions in which ischemia occurs may further include (i) myocardial infarction; (ii) trauma; and (iii) reduction or stoppage of blood flow during cardiac and/or thoracic surgery and neurosurgery, as may transpire in order to achieve the aims of such surgery. During myocardial infarct, stoppage of the heart or damage occurs which reduces the flow of blood to organs, and ischemia results. Cardiac tissue itself may also be subjected to ischemic damage. During various surgeries, reduction of blood flow, clots or air bubbles generated can lead to significant ischemic damage.

When an ischemic event occurs, there may be a gradation of injury that arises from the ischemic site. The cells at the site of blood flow restriction may undergo necrosis and form the core of a lesion. A penumbra is formed around the core where the injury is not immediately fatal but progresses slowly toward cell death. This progression to cell death may be reversed upon reestablishment of blood flow within a short time of the ischemic event.

In other embodiments of the invention a degenerative disorder may refer to any threat to the survival of, or any damage to, a cell that is present in a transfer population in, or at the host site of, a tissue transplantation procedure, prior to, during or after removal or reperfusion of cells, tissues or organs, or during storage of the cells, tissues or organs, and thus may relate to any of the cells in the body (see, e.g., U.S. Pat. Nos. 5,972,923 and 5,824,672).

By way of a brief background, preservation of the viability of cells in an organ or tissue during transplantation is often problematic. The probability that a tissue will survive the process of transplantation may depend on many factors, including the status of the tissue prior to removal, the duration of time that the tissue remains outside the body and the procedure utilized to initiate reperfusion of the tissue in the recipient. One source of injury that affects the success of tissue and organ transplantation is oxygen deprivation. Injury of organs, tissues, and cells occurs when the regular flow of oxygenated blood to the tissue and cells is interrupted. This interruption may occur during a surgical procedure to remove a transplant organ from a living or recently deceased donor, and subsequently during storage ex vivo prior to transplantation into a recipient. A particularly problematic stage in the transplantation process, for example, may be the grafting of a tissue into a recipient and reperfusion of the grafted tissue with oxygenated blood. According to non-limiting theory, when reperfusion occurs and energy metabolism resumes, free radicals may accumulate in the cells where anti-oxidant capacity has been diminished. This accumulation of free radicals may contribute to post-transplantation injury in tissue, giving rise to an increased number of damaged cells and an enhanced immune response by the recipient host. The immune response to transplanted cells may thus include an inflammatory reaction elicited by cellular antigens inappropriately exposed to the host immune system as a result of cellular damage during the implantation procedure.

Graft cells protected by the compositions and methods of the invention include those cells, tissues or organs obtained from a donor for transplantation into a recipient where the graft cells may be derived from human subjects or from animals, and may be transplanted from one subject back into the same subject or from one subject (the donor) into another subject (the recipient) for the purpose of improving the health of the recipient. The donor subject can be a living subject, fetus, or a recently deceased subject. The grafts may include replenishable cells taken from a healthy donor such as stem cells, blood cells, bone marrow cells, placental cells, liver cells, sperm, and ova. Also contemplated by the invention is the cytoprotection of cells present in one or more organs removed from a healthy donor (e.g., kidney), as well as organs containing viable cells (e.g., heart, lungs, or corneal tissue) that may, for example, be removed from a cadaver at the point of death. This last group of cells to which the cytoprotectants disclosed herein may be usefully applied includes those that may be present in fetal tissue, such as brain tissue taken from a fetus.

Tissues that may be cytoprotected using the compositions and methods of the invention may be derived from fetal tissues or from tissues of children, adolescents or adults, and may include, but are not limited to, blood and all of its components, including erythrocytes, leukocytes, platelets, and serum; central nervous tissue, including brain and spinal cord tissue, neurons, and glia; peripheral nervous tissue, including ganglia, posterior pituitary gland, adrenal medulla, and pineal tissue; connective tissue, including skin, ligaments, tendons, cartilage, bone and fibroblasts; muscle tissue, including skeletal, smooth and cardiac tissues or the cells therefrom; endocrine tissue, including anterior pituitary gland, thyroid gland, parathyroid gland, adrenal cortex, pancreas and its subparts, testes, ovaries, placenta, and the endocrine cells that are a part of each of these tissues; blood vessels, including arteries, veins, capillaries and the cells from these vessels; lung tissue; heart tissue and whole organ; heart valves; liver; kidney; intestines; bone; immune tissue, including blood cells, bone marrow and spleen; eyes and their parts; reproductive tract tissues; and urinary tract tissue. The methods of the invention may be applied, for instance, to the process of blood transfusions in which erythrocytes are transferred from an animal donor back to the donor, or to an animal recipient, or archived indefinitely. Additional applications include storage and protection of a tissue or tissue type during transplantation, for example, fetal tissue for fetal brain tissue transplants in the treatment of Parkinson's disease, the heart during transplantation, and body parts for reattachment after accidental severance.

As noted above, degenerative disorders, including degenerative diseases and related conditions, may include a wide variety of conditions associated with undesirable cell death or cell damage as a consequence of one or more of numerous potential factors. According to non-limiting theory, for example, a number of degenerative disorders as provided herein are associated with altered activity of an excitotoxic pathway leading to inappropriate cell death via apoptotic or necrotic processes. Indeed, glutamate excitotoxicity has been implicated as a mechanism in virtually all neurodegenerative diseases in which neuronal cell death is a prominent feature. Briefly, sequelae to the interaction of extracellular glutamate with the N-methyl-D-aspartate receptor (NMDA-R) include elevated cytosolic $Ca^{2+}$ levels, leading to elevated intramitochondrial $Ca^{2+}$ levels, resulting in loss of mitochondrial inner membrane potential, declining ATP production and the advent of increased reactive oxygen species (ROS), which are believed to mediate damage to cellular components and contribute to cellular mechanisms of apoptosis and necrosis. (See, e.g., Albin et al., 1992 *Neurology* 42:733-738; Danysz et al., 2000 *Neurotox. Res.* 2:85-97; Ghosh et al., 1995 *Science* 268:239; Zeron et al., 2002 *Neuron* 33:849; Albers and Beal, 2002 *Neurochem. Int.* 40(6):559-64; Vajda, 2002 *J. Clin. Neuro Sci.* 9:4-8; Greenamyre, 1986 *Arch. Neurol.* 43:1058-1062; Lees, 1993 *Neuroscience* 54:287-322; Lipton et al., 1994 *N. Engl. J. Med.* 330:613-622; Masliah et al., 1996 *Ann. Neurol.* 40:759-766; Parsons et al., 1999 *Neuropharmacol.* 38:735-767; Beal et al. (Eds.), *Mitochondria & Free Radicals in Neurodegenerative Diseases,* 1997 Wiley-Liss, Inc., N.Y.).

Hence, the presently disclosed compositions are shown herein to confer a cytoprotective effect by decreasing (e.g., with statistical significance) the activity of such an excitotoxic pathway in response to an excitotoxic stimulus, and may therefore be used to treat degenerative disorders. The present invention need not, however, be so limited, and it is contemplated that excitotoxic mechanisms or portions of excitotoxic pathways may be activated to contribute to a degenerative disorder as provided herein by stimuli other than extracellular factors such as glutamate (i.e., instead, excitotoxic mechanisms may proceed in response to intracellular events), and via signals that need not necessarily be mediated via NMDA-R or by the other classic excitotoxic pathway receptors, the kainic acid receptor (KA-R) or the a-amino-3-hydroxy-5-methyl-4-isoxazolepropionic acid (AMPA) receptor (AMPA-R).

Further according to such non-limiting theory, excitotoxic pathways contribute to specific regulation of biological processes, including those associated with cell survival, apoptosis, necrosis, proliferation and/or differentiation. In the context of the present invention "excitotoxic pathways" therefore include transient or stable associations or interactions among molecular components involved in the control of these and similar processes in cells. Depending on the particular pathway of interest, an appropriate parameter for determining induction of such a pathway may be selected. For example, for pathways associated with cell viability, there are known multiple techniques for assessing cell survival (e.g., vital dyes, metabolic indicators, etc.) and for determining apoptosis (e.g., annexin V binding, DNA fragmentation assays, caspase activation, etc.). Other aspects of excitotoxic pathways will be associated with particular cellular phenotypes, for example, altered (e.g., statistically significant increases or decreases) levels of intracellular mediators (e.g., altered levels of cyclic nucleotides or of physiologically active ionic species, in particular, divalent cations such as $Ca^{2+}$ or $Mg2^+$, etc., or of activated kinases or phosphatases), specific induction of gene expression (e.g., detectable as transcription or translation products, or by bioassays of such products, or as nuclear localization of cytoplasmic factors), or altered cellular morphology, and the like, such that cellular responsiveness to a particular stimulus (e.g., glutamate via the NMDA-R; or an agent that elevates cytosolic $Ca^{2+}$) as provided herein can be readily identified to determine whether a particular cell comprises an excitotoxic pathway.

Such pathways may, for example, be induced in a cell by a stimulus that induces or promotes ROS production. Cells may be stimulated with any one or more of a number of stimuli as provided herein, such as a cytokine, a growth factor, a hormone such as a polypeptide hormone, a cell stressor, or a peptide. Intracellular production of ROS, including hydrogen peroxide, may be determined according to established methodologies using direct or indirect ROS indicators, for example, by using fluorescent ROS indicators such as 2',7'-dichlorofluorescein diacetate ($H_2DCFDA$) or 5-(and-6)-chloromethyl-2',7'-dichlorodihydrofluorescein diacetate (CM-$H_2DCFDA$). ROS-induced DCF fluorescence can then be measured, for instance, by fluorimetry, fluorescence microscopy or flow cytofluorimetry, or according to other methods known in the art. ROS may also be detected in biological systems by any of a variety of other techniques, including spin trapping, in which a reactive radical is allowed to react with a molecular trap to produce a long-lived radical, and also including molecular fingerprinting, which measures end-products of oxidative damage. Specific compositions and methods for such trapping, as well as other means for determining ROS, are known to the art and selection of a technique for identifying ROS may depend upon the particular reactive oxygen species that is to be detected (see, e.g., Halliwell and Gutteridge, supra). Similarly, a wide variety of means for determining alterations (e.g., statistically significant increases or decreases) in intracellular $Ca^{2+}$ levels, including means for distinguishing between altered mitochondrial $Ca^{2+}$ levels and altered cytosolic $Ca^{2+}$ levels, are described herein and known to the art (e.g., Haugland, *Handbook of Fluorescent Probes and Research Products—9$^{th}$ Ed.,* 2002 Molecular Probes, Inc., Eugene, Oreg.).

Affinity techniques are particularly useful in the context of the present invention, which contemplates methods for identifying cell-derived molecular components that interact specifically and/or selectively with the cytoprotective compounds disclosed herein. In particular, immobilized (e.g., retained on a solid phase such as a glass, plastic, polymeric, metal, crosslinked polysaccharide or other substrate, for instance, a plate, well, bead, mesh, column, filter, resin, membrane or the like, via covalent or non-covalent attachment), detectably labeled (e.g., covalently or non-covalently attached to or associated with a readily detectable moiety such as a fluorophore, chromophore, radionuclide, quantum dot, enzyme, hapten, epitope, affinity domain such as avidin, biotin, or streptavidin, protein A, protein G or the like, or another detectable moiety) or retrievably tagged (e.g., covalently or non-covalently attached to or associated with a readily recoverable moiety, such as a magnetic or paramagnetic particle, an affinity domain such as polyhistidine, glutathione or glutathione-S-transferase, maltose-binding protein, lectin, oligosaccharide, avidin, biotin, or streptavidin, protein A, protein G or the like, a hapten or epitope tag such as a myc, FLAG®, hemagglutinin, or other monoclonal antibody-defined epitope tag, etc.) derivatives of the presently disclosed cytoprotective compounds may be used as affinity ligands to which interacting cell-derived molecular components may bind under suitable conditions. Related embodiments therefore may include any method that exploits a specific binding interaction between a cytoprotective compound and a cell-derived molecular component such as a protein or peptide, lipid (including phospholipids, glycolipids and other lipids), nucleic acid (including DNA and RNA), carbohydrate (including oligosaccharides and polysaccharides and their derivatives), metabolite, intermediate, cofactor or the like, to effect the isolation of the cellular component. See, for example, Scopes, R. K., *Protein Purification: Principles and Practice,* 1987, Springer-Verlag, N.Y.; Weir, D. M., *Handbook of Experimental Immunology,* 1986, Blackwell Scientific, Boston; Deutscher, M. P., *Guide to Protein Purification,* 1990, Methods in Enzymology Vol. 182, Academic Press, New York; and Hermanson, G T. et al., *Immobilized Affinity Ligand Techniques,* 1992, Academic Press, Inc., California; which are hereby incorporated by reference in their entireties, for details regarding affinity techniques for isolating and characterizing cell-derived components, for example, proteins and peptides.

The term "isolated" means that the material is removed from its original environment (e.g., the natural environment if it is naturally occurring). For instance, a naturally occurring protein or peptide present in a living animal is not isolated, but the same protein or peptide, separated from some or all of the co-existing materials in the natural system, is isolated. Thus, for example, such proteins could be part of a multisubunit complex or a membrane vesicle, and/or such peptides could be part of a composition, and still be isolated in that such complex, vesicle or composition is not part of its natural environment. Accordingly, certain embodiments as provided herein contemplate a method for isolating a molecular component of an excitotoxic pathway, comprising contacting a biological sample with a compound having a structure disclosed herein under conditions and for a time sufficient to permit a binding interaction between the compound and the molecular component, and thereby isolating the pathway component. Related embodiments provide determination of altered structure or altered biological activity of such a component, preferably in situations where such an alteration is a cause, consequence, or correlate of a degenerative disorder as described herein. Such isolation and characterization of excitotoxic pathway molecular components are expected to provide useful information for the determination of a risk for having or presence of a degenerative disorder in a subject, and also for the development of additional therapeutics. Structural characterization of an isolated component is within the available methodologies of the art. For instance, in the case of a protein or peptide, those familiar with the art will be aware of a variety of techniques for identifying and isolating a polynucleotide that is capable of encoding and directing the biological expression of such polypeptide. (e.g., Ausubel et al., *Current Protocols in Molecular Biology*, 2003 Wiley & Sons, NY; Sambrook et al., *Molecular Cloning—A Laboratory Manual-3$^{rd}$ Ed.*, 2001 Cold Spring Harbor Laboratory, Cold Spring Harbor, N.Y.).

Biological samples may comprise any tissue or cell preparation. Biological samples may be provided by obtaining a blood sample, biopsy specimen, tissue explant, organ culture or any other tissue or cell preparation from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortal, immortalized or immortalizable cell lines (e.g., capable of at least ten cell doublings in vitro), somatic cell hybrid or cytoplasmic hybrid "cybrid" cell lines (including mitochondrial cybrid cells having nuclear and mitochondrial DNAs of differing biological origins, see, e.g., U.S. Pat. No. 5,888,498 and International Publication No. WO 95/26793), differentiated or differentiatable cell lines, transformed cell lines and the like. In certain preferred embodiments of the invention, the subject or biological source may be suspected of having or being at risk for having a degenerative disorder, for instance, a disease associated with altered activity of an excitotoxic pathway, including, for example, altered mitochondrial function (see, e.g., U.S. Pat. No. 6,140,067), or oxidative modification of one or more cellular proteins, and in certain preferred embodiments of the invention the subject or biological source may be known to be free of a risk or presence of such a disease. In certain other preferred embodiments, a biological sample comprises a cybrid cell line having nuclear and mitochondrial DNAs of differing biological origins, which in certain embodiments may be a human cell, an immortal cell, a neuronal cell, a neuroblastoma or other transformed cell, for example, a SH-SY5Y human neuroblastoma cell. In certain other particularly preferred embodiments, a biological sample comprises a sample readily obtained from a subject or biological source, such as blood, skin, skeletal muscle, liver or cartilage.

"Biological activity" of a cell-derived molecular component, for instance, a protein, may be any detectable parameter that directly relates to a condition, process, pathway, dynamic structure, state or other activity involving the component and that permits detection of altered component function in a biological sample from a subject or biological source. The methods of the present invention thus pertain in part to such correlation where the component having biological activity may be, for example, an enzyme, a structural protein, a receptor, a ligand, a membrane channel, a regulatory protein, a subunit, a complex component, a chaperone protein, a binding protein or a protein having a biological activity according to other criteria including those provided herein. Such activity may include the amount of a cell-derived molecular component that is present, or the amount of a given component's function that is detectable. "Altered biological activity" of a cell-derived molecular component may refer to any condition or state, including those that accompany a degenerative disorder, for example, a disease or disorder characterized by detectably altered (e.g., increased or decreased in a statistically significant manner relative to an appropriate control) biological activity of one or more such components or by altered cell viability or constitution, by altered activity of an excitotoxic pathway, or by modification of an excitotoxic pathway molecular component as provided herein.

Altered biological activity of a protein or peptide may have its origin in deletion, substitution or insertion of one or more amino acids in the protein; in posttranslational modification of the protein; in an altered expression level (e.g., a statistically significant increase or decrease in the amount present) of a protein; in oxidatively modified structures or oxidative events as well as in oxidation-independent structures or events, in direct interactions between genes and/or their gene products, or in structural or functional changes that occur as the result of interactions between intermediates that may be formed as the result of such interactions, including metabolites, catabolites, substrates, precursors, cofactors and the like. According to certain embodiments as provided herein, altered biological activity of a protein may also result from direct or indirect interaction of a biologically active protein with an introduced agent such as any of the cytoprotective compounds disclosed herein.

Additionally, altered biological activity may result in altered respiratory, metabolic or other biochemical or biophysical activity in some or all cells of a biological source having a degenerative disorder. As non-limiting examples, markedly impaired mitochondrial electron transport chain (ETC) activity may be related to altered biological activity of at least one protein, as may be generation of increased free radicals such as reactive oxygen species (ROS) or defective oxidative phosphorylation. As further examples, altered mitochondrial membrane potential, induction of apoptotic pathways and formation of atypical chemical and biochemical crosslinked species within a cell, whether by enzymatic or non-enzymatic mechanisms, may all be regarded as indicative of altered biological activity which may contribute to altered activity of an excitotoxic pathway.

Relevant biological activities that may be altered in a degenerative disorder will be known to those having familiarity with particular degenerative disorders in view of the present disclosure. For example, in the context of combination therapy for a distinct degenerative disorder, osteoporosis, certain estrogen receptor genotypes along with genotypes for vitamin D receptor genotype and for apolipoprotein E have been associated with sensitivity to a therapeutic regimen that includes estrogen (see U.S. Pat. No. 6,566,064). As such, these genotypes may represent altered biological activities having relevance to one or more degenerative disorders. In the context of neurodegenerative disorders, as another example, a biomarker as disclosed in U.S.

Application Publication No. 2003/0129134 may provide a relevant altered biological activity. Additional examples having specific relevance to Alzheimer's disease include whether a human female subject at risk for developing such disease has at least one ApoE4 allele. Responsiveness of such subjects to other distinct estrogen compounds and the correlation of such responsiveness with an ApoE4 genotype are described in U.S. Pat. No. 6,432,643 and in U.S. Application Publication No. 2002/0102725.

Therapeutic Methods

In another embodiment, the present invention provides a method for treating a degenerative disorder. Such methods include administering a compound of the present invention to a warm-blooded animal in an amount sufficient to treat the condition. In this context, "treat" includes prophylactic administration. Accordingly, in certain specific related embodiments the invention contemplates a method for treating (i) a neurodegenerative disorder (e.g., Alzheimer's disease, mild cognitive impairment, Parkinson's disease, amyotrophic lateral sclerosis, multiple sclerosis), (ii) an ophthalmic disease (e.g., glaucoma, retinitis pigmentosa, macular degeneration, elevated intraocular pressure, or Leber's hereditary optic neuropathy), (iii) a cardiovascular disease (e.g., stroke, ischemia or myocardial infarction), (iv) a disorder of bone, joint, connective tissue or cartilage (e.g., osteoarthritis, rheumatoid arthritis or psoriatic arthritis, (v) a disorder associated with altered activity of an excitotoxic pathway, (vi) tissue transplantation or (vi) a mitochondrial disorder (e.g., Friedreich's ataxia). Such methods include systemic administration of a compound of the present invention, preferably in the form of a pharmaceutical composition as discussed below. As used herein, systemic administration includes oral and parenteral methods of administration. For oral administration, suitable pharmaceutical compositions of the compounds of the present invention include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to a compound of structure (I), buffers, antioxidants, bacteriostats, and other additives commonly employed in such solutions.

In the practice of the methods of this invention, compounds of structure (I) are typically administered to a patient in the form of a pharmaceutically acceptable composition, which comprises one or more compounds of structure (I) in combination with one or more pharmaceutically acceptable carrier(s). "Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Because of the lipophilicity of compounds of structure (I), lipophilic solvents are preferred carriers and/or may be components of preferred carriers. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The present invention also expressly contemplates, in certain embodiments, compositions and methods of treatment that include, in combination, (i) as a first cytoprotective compound, at least one of the compounds of structure (I) as described herein, in place of an estrogen or estrogen derivative, analogue or homologue; along with (ii) at least one second compound that may be an antioxidant (e.g., glutathione and other antioxidants disclosed in U.S. Pat. No. 5,972,923, also, e.g., ascorbate, uric acid, alpha-tocopherol, beta-carotene, flavonoids, desferrioxamine, see also, e.g., Halliwell and Gutteridge, Free Radicals in Biology and Medicine, 1999 Oxford Univ. Press, N.Y.); an antiestrogen (e.g., U.S. Pat. No. 6,677,324, see also, e.g., Buzdar, 2005 *Clin. Canc. Res.* 11:906s, McDonnell, 2005 *Clin. Canc. Res.* 11:871s (TAS-108), Eng-Wong et al., 2004 *Expert Rev. Anticanc. Ther.* 4:523 (raloxifene), Gradishar, 2004 *Oncologist* 9:378 (tamoxifen); Lord et al. 2002 *Altern Med Rev* 7:112 (2-hydroxyestrone and 2-hydroxyestradiol); a hormone (e.g., gonadotropin, gonadotropin releasing hormone, melatonin (e.g., U.S. Application Publication No. 2004/0223963), relaxin (e.g., U.S. Pat. No. 6,251,863, Conrad et al. 2004 *Am J Physiol Regul. Integr Comp Physiol* 287: R250, Hayes 2004 *Reprod Biol Endocrinol* 2:36)); a mineral (e.g., calcium, magnesium); a vitamin (e.g., Vitamin D, Vitamin E, selenium, folic acid, Vitamin B6, Vitamin B12); calcium-plus-vitamin D (e.g., U.S. Application Publication No. 2003/0045510); a neuropeptide (e.g., a neurotrophin (e.g., U.S. Pat. No. 5,990,078), or a growth factor such as a nerve growth factor); a cholesterol-lowering agent such as a statin (e.g., U.S. Application Publication No. 2004/0259886) or niacin (e.g., inositol hexanicotinate); an Alzheimer's disease-treating agent such as probucol or an analog of probucol (see e.g., U.S. Pat. No. 6,274,603, Tardif et al., 2003 *Curr Opin Lipidol.* 14:615), AGI-1067 (Doggrell 2003 *Expert Opin Invest Drugs* 12:1855, Tardif 2003 *Am J Cardiol* 91:41A; Wasserman 2003 *Am J Cardiol* 91:34A), tacrine (including pulsed-release and/or timed-release dosages, see, e.g., U.S. Pat. No. 6,036,973), Donepezil hydrochloride (Aricept™), memantine HCl (e.g., Namenda®), an acetylcholinesterase inhibitor (e.g., huperzine A, galanthamine, other polyamines, see, e.g., Du et al 2004 *Curr Pharm Des.* 10:3141); a stroke-treating agent (e.g., tissue plasminogen activator, tPA, magnesium); a therapeutic antibody (e.g., Abciximab (ReoPro™), natalizumab (Tysabri®), adalimumab (Humira®), infliximab (Remicade®), efalizumab (Raptiva®) or other therapeutic antibodies); a cruciferous indole compound (e.g., U.S. Pat. No. 6,605,605), including brassinins, camalexins, and phytoalexins (Ruszkowska et al., 2003 *Adv Exp Med Biol* 527:629), indole-3-carbinol (I3C) and 3,3'-diindolylmethane (DIM) (Leibelt et al. 2003 *Toxicol. Sci* 74:10); a sterol or 5-alpha-stanol absorption inhibitor (e.g., U.S. Application Publication No. 2003/0119796), or an agent that treats an amyloid-P disease, neurodegeneration or cellular toxicity (see, e.g., U.S. Application Publication No. 2005/0031651); and, optionally in certain embodiments, (iii) a pharmaceutically acceptable carrier. In certain such embodiments and according to non-limiting theory, the first cytoprotective compound and the second compound may, upon administration either together in combination or separately, result in a synergistic effect (e.g., an effect that is greater, with statistical significance, than that which results from administration of either compound alone), and in certain other such embodiments the first and second compounds may result in an additive or less-than-additive effect, but these invention embodiments are not intended to be so limited, such that for certain such embodiments an unexpected advantage is afforded by the availability of the herein disclosed first cytoprotective compound(s) of structure (I) in a form that can be administered conveniently and concurrently with the the second compound.

The pharmaceutical compositions that contain one or more compounds as provided herein may be in any form which allows for the composition to be administered to a patient. For example, the composition may be in the form of a solid, liquid or gas (aerosol). Typical routes of administration include, without limitation, oral, topical (including transdermal and ophthalmic, for example in the form of a patch), parenteral (e.g., sublingually or buccally), sublingual, rectal, vaginal, and intranasal. The term parenteral as used herein includes subcutaneous injections, intravenous, intraarterial, intramuscular, intradermal, intrasternal, intracavernous, intraperitoneal, intrathecal, intraocular, retroorbital, intrameatal, intraurethral injection, infusion techniques or electrically assisted delivery methods, such as electroporation or iontophoresis. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, which is the route of administration in certain embodiments, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, the compositions may contain, in addition to one or more compounds of structure (I), one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a representative adjuvant. An injectable pharmaceutical composition is preferably sterile.

A liquid composition intended for either parenteral or oral administration should contain an amount of a compound as provided herein such that a suitable dosage will be obtained. Typically, this amount is at least 0.01 wt % of the compound in the composition. When intended for oral administration, this amount may be varied to be between 0.1 and about 70% of the weight of the composition. Representative oral compositions contain between about 4% and about 50% of the compound(s). Representative compositions and preparations are prepared so that a parenteral dosage unit contains between 0.01 to 1% by weight of the compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or device for electrically-assisted delivery, such as electroporation or iontophoresis device. Topical formulations may contain a concentration of the compound of from about 0.1 to about 10% w/v (weight per unit volume).

The composition may be intended for rectal administration, in the form, e.g., of a suppository that will melt in the rectum and release the drug. The composition for rectal administration may contain an oleaginous base as a suitable nonirritating excipient. Such bases include, without limitation, lanolin, cocoa butter and polyethylene glycol. In the methods of the invention, the compound of structure (I) as described herein may be administered through use of insert(s), bead(s), timed-release formulation(s), patch(es) or fast-release formulation(s).

It will be evident to those of ordinary skill in the art that the optimal dosage of the compound(s) may depend on the weight and physical condition of the patient; on the severity and longevity of the physical condition being treated; on the particular form of the active ingredient, the manner of administration and the composition employed. The use of the minimum dosage that is sufficient to provide effective therapy with minimal or no feminizing effects is usually preferred. Patients may generally be monitored for therapeutic or prophylactic effectiveness, as well as for feminizing effects, using assays suitable for the condition being treated or prevented and assays suitable for measuring feminizing activity, which will be familiar to those having ordinary skill in the art. Suitable dose sizes will vary with the size, condition and metabolism of the patient, and according to the sex of the patient, in some cases, but will typically range from about 10 mL to about 500 mL for 10-60 kg individual. It is to be understood that according to certain embodiments the compound may be membrane permeable, preferably permeable through the plasma membrane and/or through mitochondrial outer and/or inner membranes. According to certain other embodiments, the use of the compound as disclosed herein can involve such an agent being bound to another compound, for example, a monoclonal or polyclonal antibody, a protein or a liposome, which assist the delivery of said compound to a desired target location.

The following Examples illustrate the invention and are not intended to limit the same. Those skilled in the art will recognize, or be able to ascertain through routine experimentation, numerous equivalents to the specific compounds and procedures described herein. Such equivalents are considered to be within the scope of the present invention.

EXAMPLES

Example 1

Synthesis of a Representative Compound of Structure (I)

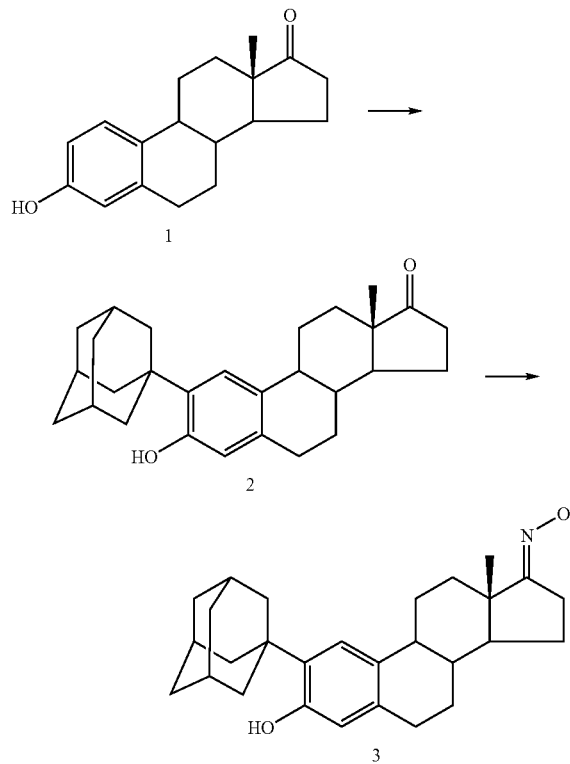

Synthesis of Compound No. 2

To a stirred suspension of estrone (compound no. 1) (1.08 g) and 1-adamantanol (0.70 g) in hexane (30 ml) at 0° C. under an argon atmosphere was added $BF_3 \cdot Et_2O$ (1.6 ml) dropwise via a syringe. The mixture was stirred and allowed to warm to room temperature over a period of 4 hours. The solvent was then removed under vacuum. The residue was titrated with water. The resulting solid was collected by filtration and recrystallized from a mixed solvent of ethyl acetate and hexane to yield compound no. 2 as a white solid (0.792 g). $^1H$ NMR (CDCl$_3$) d=7.14(s, 1H), 6.41(s, 1H), 4.68(s, 1H), 2.81(m, 2H), 2.48(m, 2H), 2.25(m, 2H), 2.0-10(m, 8H), 1.95(m, 2H), 1.77(s, 5H), 1.58(m, 6H), 1.43(m, 2H), 1.25(m, 1H), 0.91(s, 3H) ppm.

Synthesis of Compound No. 3

To a solution of compound no. 2 (0.202 g) in methanol (20 ml) was added hydroxylamine hydrochloride (0.350 g) and pyridine (2.0 ml). The mixture was refluxed for 17 hours. The mixture was then titrated with water. The resulting solid was collected by filtration and dried under high vacuum to yield compound no. 3 as a white solid (0.167 g). LC-MS cacld. for $C_{28}H_{37}NO_2$: 419; found: 420.

Example 2

Synthesis of Further Representative Compounds

Using the procedure set forth in Example 1 for the synthesis of compound no. 2, the following compounds were also prepared.

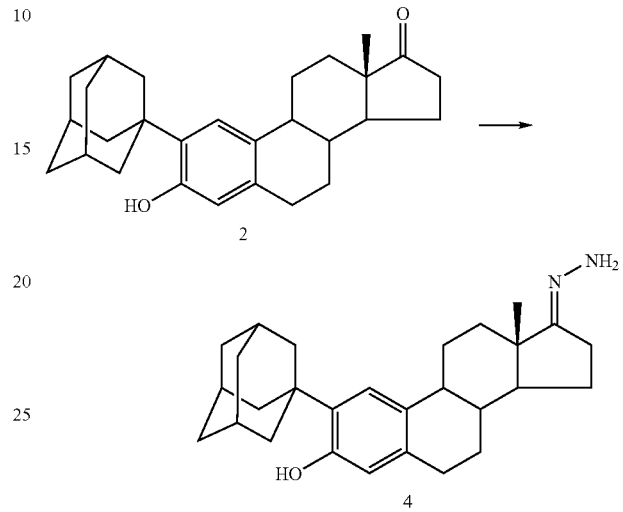

Synthesis of Compound No. 4

To a solution of compound no. 2 (0.202 g) in ethanol (10 ml) was added hydrazine (1.0 ml). The mixture was refluxed for 17 hours, and the solvent was then removed under vacuum. The residue was purified on a silica gel column using 2.5% methanol in dichloromethane to yield compound no. 4 as a white solid (0.172 g). LC-MS: cacld. for $C_{28}H_{38}N_2O$: 418; found: 419. $^1H$ NMR (CDCl$_3$) d=7.15(s, 1H), 6.40(s, 1H), 5.16(bs, 1H), 4.80(bs, 2H), 2.78(m, 3H), 2.50-1.20(m, 27H), 0.89(s, 3H) ppm.

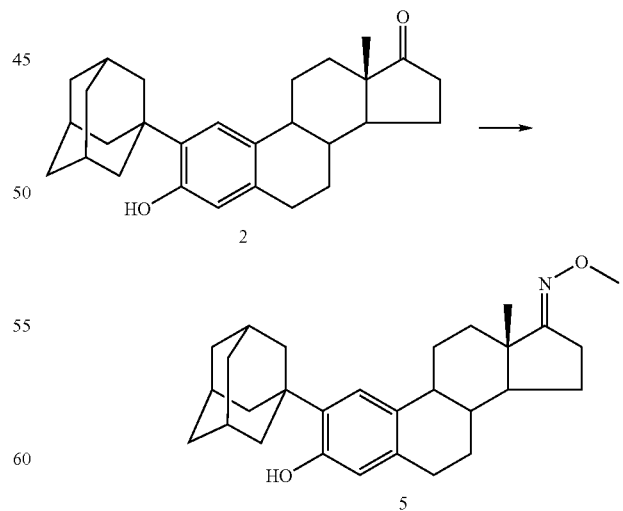

Synthesis of Compound No. 5

To a solution of compound no. 2 (0.202 g) in methanol (10 ml) was added O-methyl hydroxylamine hydrochloride (0.415 g) and pyridine (1.0 ml). The mixture was refluxed for 17 hours. The solvent was then removed under vacuum. The residue was dissolved in ethyl acetate and washed with brine. The crude product was purified on a silica gel column using 10% ethyl acetate in hexane to yield compound no. 5 as a pale yellow solid (0.197 g). LC-MS: cacld. for $C_{29}H_{39}NO_2$: 433; found: 431. $^1$H NMR (CDCl$_3$) d=7.15(s, 1H), 6.40(s, 1H), 4.18(bs, 1H), 3.85(s, 3H), 2.78(m, 3H), 2.51-1.27(m, 27H), 0.94(s, 3H) ppm.

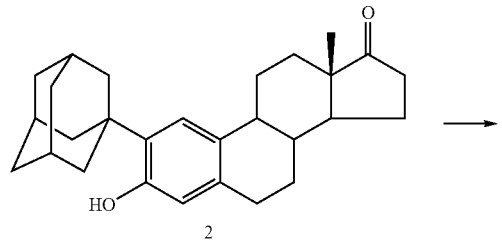

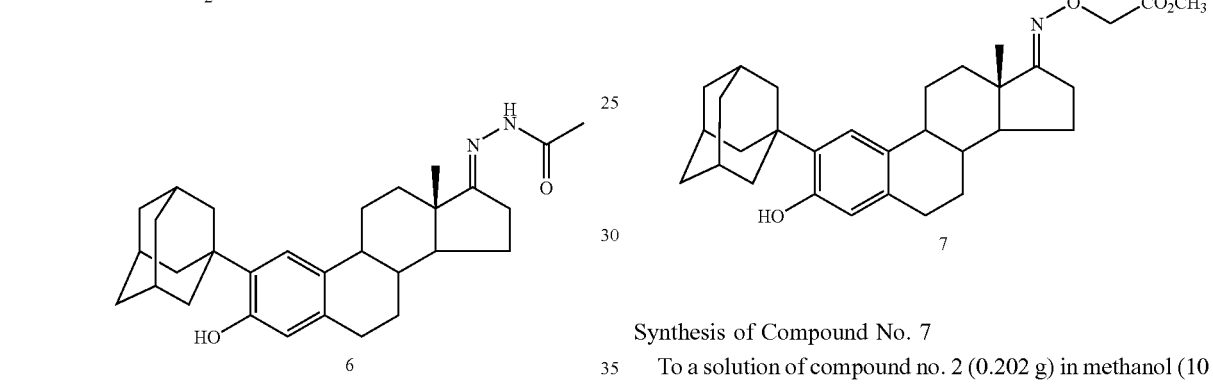

Synthesis of Compound 6

To a solution of compound no. 2 (0.100 g) in ethanol (10 ml) was added acetohydrazide (0.185 g). The mixture was refluxed for 18 hours. The mixture was then titrated with water. The resulting solid was collected by filtration, washed with water, and dried under high vacuum to yield a white solid (0.102 g). LC-MS: cacld. for $C_{30}H_{40}N_2O_2$: 460; found: 483 (M+Na).

Example 3

Synthesis of Further Representative Compounds, Affinity Resins and Biotin Derivatives

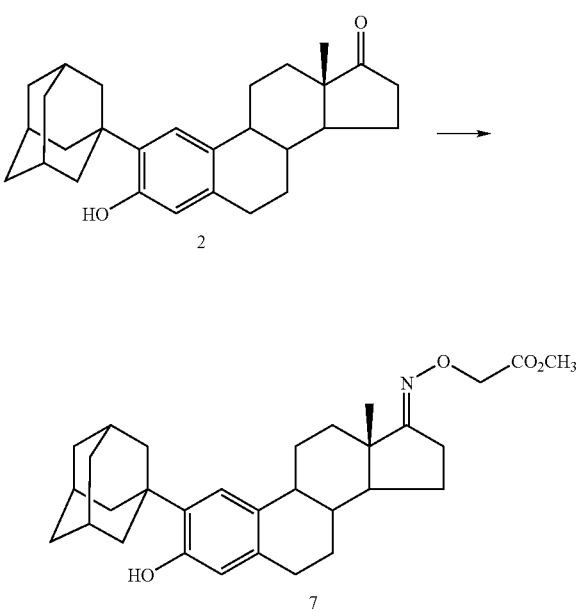

Synthesis of Compound No. 7

To a solution of compound no. 2 (0.202 g) in methanol (10 ml) was added carboxymethoxylamine hemihydrochloride (0.370 g). The mixture was refluxed for 18 hours. The mixture was then diluted ethyl acetate and washed with saturated NaHCO$_3$ (aq.), brine, and then dried over sodium sulfate. The crude product was purified on a silica gel column using 20% ethyl acetate in hexanes as the eluent to give compound no. 7 as a white solid (0.198 g). $^1$H NMR (CDCl$_3$) d=7.13(s, 1H), 6.40(s, 1H), 4.83(bs, 1H), 4.61(s, 2H), 3.76(s, 3H), 2.77(m, 2H), 2.60(m, 2H), 2.39(m, 1H), 2.25(m, 1H), 2.10(m, 11H), 1.90(m, 3H), 1.63-1.36(m, 8H), 0.93(s, 3H) ppm.

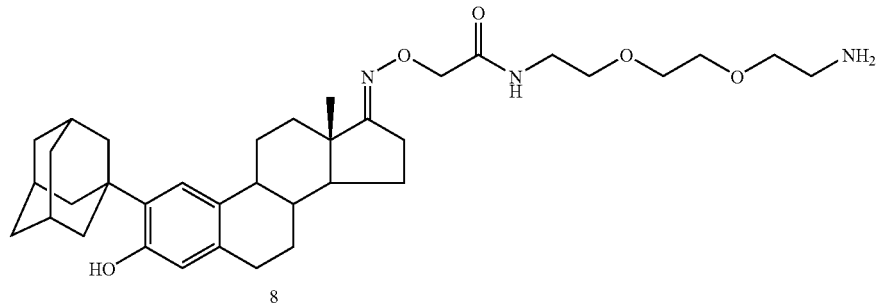

8

Synthesis of Compound No. 8

A solution of compound no. 7 (40 mg) and 2,2'-(ethylenedioxy)bis(ethylamine) (100 mg) in methanol (2 ml) was refluxed for 18 hours. The mixture was diluted with ethyl acetate and washed with water (5×) and dried over sodium sulfate to yield compound no. 8 as a white solid. The crude product was analytically pure. LC-MS: cacld. for $C_{36}H_{53}N_3O_5$: 607; found: 608.

Synthesis of Affinity Resin No. 9

NHS activated-sepharose resin (20 ml) was washed with NMP (4×) and shaken with a solution of compound no. 8 (6.1 mg) in NMP (20 ml) and DIEA (1 ml) at room temperature for 4 hours. LC-MS indicated complete disappearence of compound no. 8 in the solution. Ethanolamine (1 ml) was added, and the mixture was shaken for 18 hours

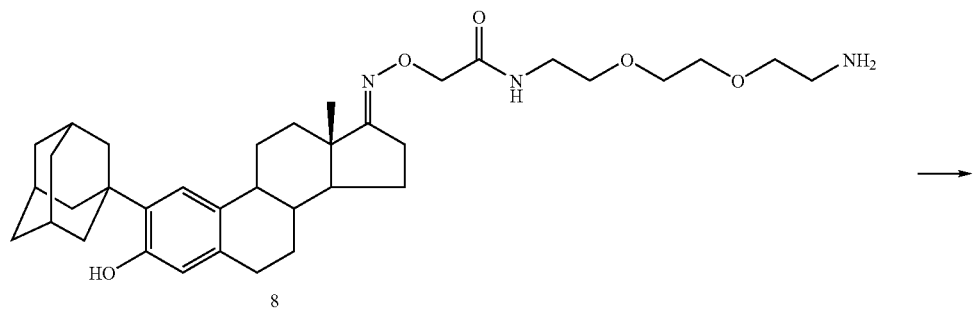

8

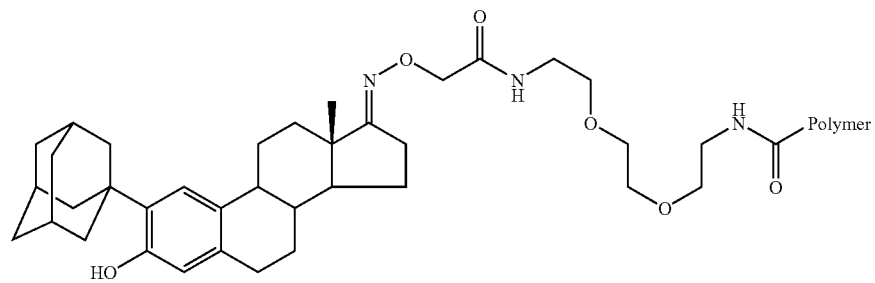

9 to yield affinity resin no. 9, which was then washed with methanol (3×), NMP (3×) and methanol (3×).

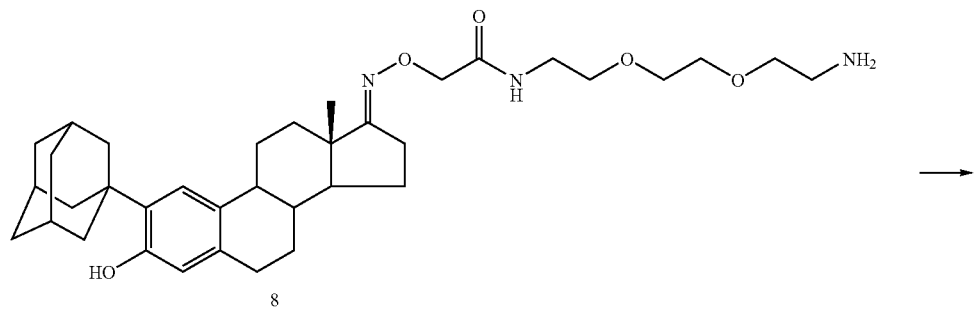

8

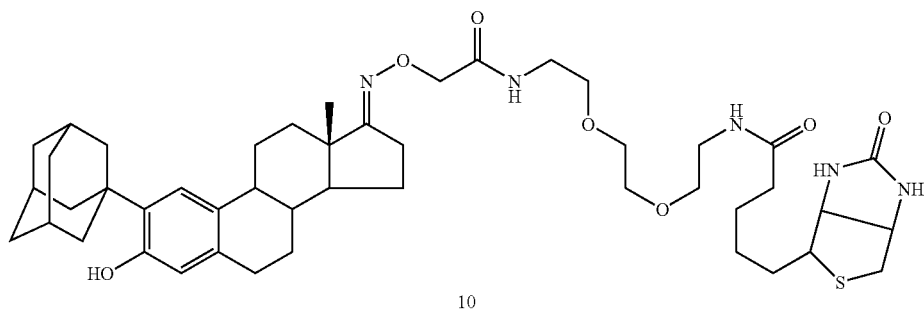

10

Synthesis of Biotin Derivative No. 10

Compound no. 8 (0.179 g, 0.29 mmole) was dissolved in DCM/DMF (1/1, 20 ml). DIEA (1 ml) and biotin-NHS ester (60 mg) were added. The mixture was stirred at room temperature for 18 hours. The solvent was removed under vacuum. The residue was purified on RP-HPLC to yield biotin derivative no. 10 as an off-white solid (0.123 g). LC-MS: calcd. for $C_{46}H_{67}N_5O_7S$: 833; found: 834.

Example 4

Synthesis of Further Compounds

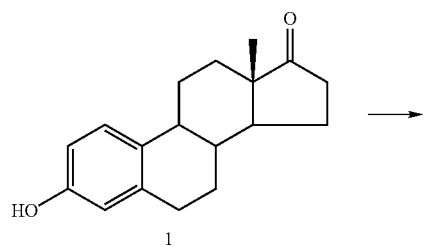

1

-continued

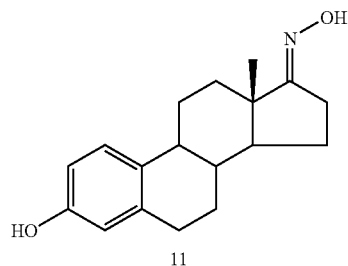

11

Synthesis of Compound No. 11

To a solution of estrone (compound no. 1) (0.540 g) in methanol (20 ml) was added hydroxylamine hydrochloride (0.690 g) and pyridine (2.0 ml). The mixture was refluxed for 17 hours. The mixture was then titrated with water. The resulting solid was collected by filtration and dried under high vacuum to yield compound no. 11 as a white solid (0.167 g). LC-MS: cacld. for $C_{18}H_{23}NO_2$: 285; found: 286. $^1$H NMR (CDCl$_3$) d=9.14(bs, 1H), 7.90(s, 1H), 7.08(d, 1H), 6.58(d, 1H), 6.52(s, 1H), 3.31(s, 1H), 2.84(m, 3H), 2.46(m, 2H), 2.35(m, 1H), 2.20(m, 1H), 2.05(s, 1H), 1.93(m, 2H), 1.50(m, 4H), 0.91(s, 3H) ppm.

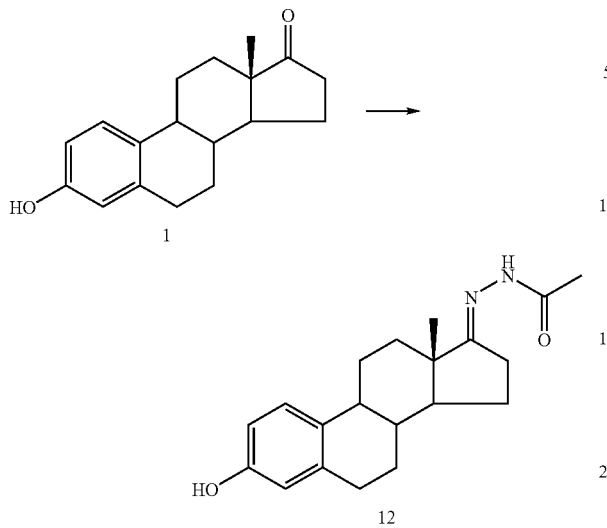

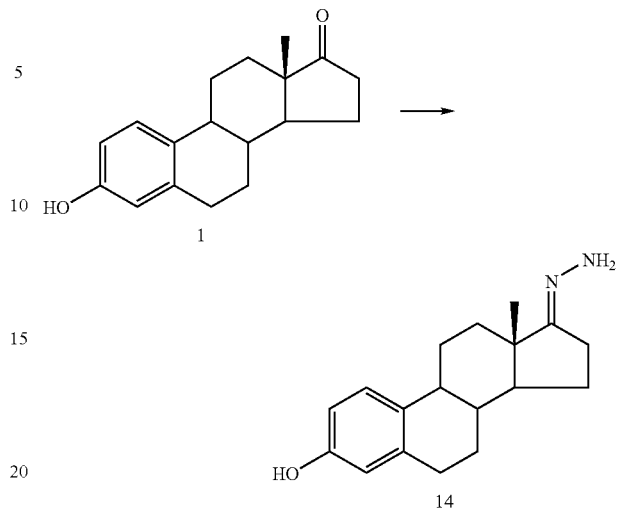

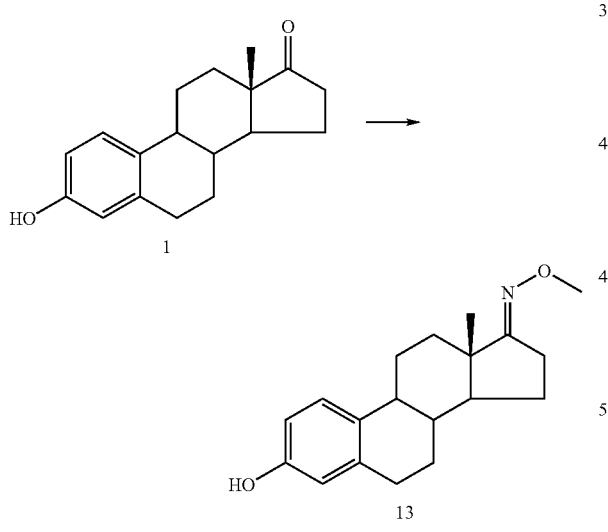

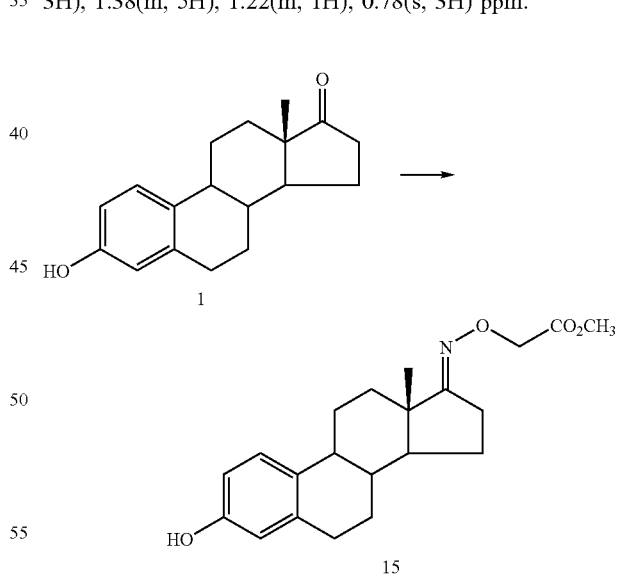

Synthesis of Compound No. 12

To a solution of estrone (compound no. 1) (0.540 g) in ethanol (20 ml) was added acetohydrazide (0.740 g) and pyridine (2.0 ml). The mixture was refluxed for 18 hours. The mixture was then titrated with water. The resulting solid was collected by filtration, washed with water and dried under high vacuum to give compound no. 12 as a white solid (0.616 g). LC-MS: cacld. for $C_{20}H_{26}N_2O_2$: 326; found: 327. $^1$H NMR showed a mixture of two rotamers.

Synthesis of Compound No. 13

To a solution of estrone (compound no. 1) (0.540 g) in ethanol (20 ml) was added O-methyl-hydroxylamine (0.835 g) and pyridine (2.0 ml). The mixture was refluxed for 18 hours. The mixture was then titrated with water. The resulting solid was collected by filtration, washed with water and dried under high vacuum to give compound no. 13 as a white solid (0.576 g). LC-MS: cacld. for $C_{19}H_{25}NO_2$: 299; found: 300. $^1$H NMR (CDCl$_3$/DMSO) d=8.25(s, 1H), 6.79(s, 1H), 6.31(s, 1H), 6.25(s, 1H), 3.51(s, 3H), 2.60(m, 3H), 2.25(m, 4H), 1.65(m, 3H), 1.18(m, 6H), 0.63(s, 3H) ppm.

Synthesis of Compound No. 14

To a solution of estrone (compound no. 1) (0.540 g) in ethanol (20 ml) was added hydrazine monohydrate. The mixture was refluxed for 18 hours. The mixture was then titrated with water. The resulting solid was collected by filtration, washed with water, and dried under high vacuum to yield compound no. 14 as a white solid (0.552 g). LC-MS: cacld. for $C_{18}H_{24}N_2O$: 284; found: 285. $^1$H NMR (DMSO) d=8.98(s, 1H), 7.04(d, 1H), 6.50(dd, 1H), 6.44(d, 1H), 5.33(s, 2H), 2.73(m, 2H), 2.25(m, 2H), 2.12(m, 2H), 1.85(m, 3H), 1.38(m, 5H), 1.22(m, 1H), 0.78(s, 3H) ppm.

Synthesis of Compound No. 15

To a solution of estrone (compound no. 1) (0.540 g) in methanol (25 ml) was added carboxymethoxylamine hemihydrochloride (1.10 g). The mixture was refluxed for 17 hours. The mixture was then diluted with water. The resulting solid was collected by filtration and dried under high vacuum to give compound no. 15 as a white solid (0.700 g). $^1$H NMR (CDCl$_3$) d=7.13(d, 1H), 6.62(d, 1H), 6.56(s, 1H), 5.20(bs, 1H), 4.60(dd, 2H), 3.76(s, 3H), 2.82(m, 2H), 2.60 (m, 2H), 2.00(m, 1H), 1.88(m, 2H), 1.59(m, 2H), 1.40(m, 6H), 0.93(s, 3H) ppm.

Example 5

Cytoprotective Activity

This Example describes experiments demonstrating cytoprotective activity of compounds synthesized according to Examples 1 and 2 above, using cerebellar granule cells and cortical neurons.

Preparation of Cerebellar Granule Cells. Cultured cerebellar granule cells were prepared as described previously (Courtney et al., 1990 *J. Neurosci.* 10:3873-3879) from 7 day postnatal Wistar rats. Cells were plated on poly-D-lysine-coated 10 cm diameter plastic tissue culture dishes at a seeding density of $1 \times 10^6$ cells per ml. Cells were cultured in minimal essential medium (MEM) containing Earles salts (GIBCoBRL/Life Technologies, Inc., Grand Island, N.Y.) plus 10% (vol/vol) fetal calf serum, 25 mM KCl, 30 mM glucose, 2 mM glutamine, 100 μg/ml streptomycin, and 100 U/ml penicillin (incubation medium). After 24 hours 10 mM cytosine arabinoside was added to inhibit non-neuronal cell proliferation. Cells were maintained at 37° C. in a humidified atmosphere of 5% $CO_2$/95% air and were used after 7-8 days in vitro.

Cortical Neurons. Primary cultures of rat cortical neurons expressing endogenous NMDA receptors were prepared essentially as described by Stout et al. (1998 *Nat. Neurosci.* 1:366-373).

Fluorometric $Ca^{2+}$ Measurements. Cytoplasmic $Ca^{2+}$ was measured in neurons cultured in 96-well plates using magfluo-4, a cell permeant low affinity $Ca^{2+}$ dye (Molecular Probes, Inc., Eugene, Oreg.). Prior to experimental determination of calcium by fluorescence detection, cells were exposed for 24 hours either to a test cytoprotective compound (10 μM) or vehicle control. A stock solution of magfluo-4 (1 mg/ml) was prepared on the day of experiment in DMSO and then diluted in HBSS to a final concentration of 4 μM. The culture medium was carefully aspirated, and cells were loaded with the dye (100 μl of 4 μM solution per well) for 25 minutes in the incubator (37° C. in a humidified atmosphere of 5% $CO_2$/95% air). Then the loading buffer was replaced with dye-free HBSS and the plates were assayed by continuous monitoring for approximately 20-30 minutes in a fluorescent plate reader (FLIPR, Molecular Devices, Inc., Sunnyvale, Calif.) according to the manufacturer's instructions at 488 nM (excitation) and 525 nm (emission).

After baseline measurements were established, cells were exposed to 100 μM glutamate and 10 μM glycine in a HEPES-buffered salt solution (HBSS) containing 137 mM NaCl, 5 mM KCl, 10 mM $NaHCO_3$, 20 mM HEPES, 5.5 mM glucose, 0.6 mM $KH_2PO_4$, 1.4 mM $CaCl_2$, 0.9 mM $MgSO_4$ while fluorescence monitoring continued. Approximately 10 minutes following the glutamate addition, EGTA was added and fluorescence monitoring continued. After about 3 minutes the mitochondrial uncoupler FCCP was added (final concentration<1 μM) and fluorescence readings continued.

Relative to the cytoplasmic $Ca^{2+}$ signals that were detected in the vehicle control group, by approximately 3 minutes following the addition of glutamate, cells that had been pretreated with compounds of the invention consistently exhibited significantly reduced levels of cytoplasmic $Ca^{2+}$. By reducing such intracytoplasmic $Ca^{2+}$ levels, both necrosis and apoptosis resulting from excitotoxicity were correspondingly reduced. After addition of EGTA, cytoplasmic $Ca^{2+}$ levels for all groups dropped to below baseline, and following administration of FCCP cytoplasmic $Ca^{2+}$ was again detectable, reflecting, according to nonlimiting theory, release by mitochondria of $Ca^{2+}$ that had been sequestered there during the course of the cellular response to glutamate. Lower levels of $Ca^{2+}$ release were observed following FCCP treatment in cells pretreated with invention compounds relative to control cells, corroborating repression by the compounds of the detectable intracytoplasmic Ca2+ accumulations at earlier timepoints, as described above.

$^{45}Ca^{2+}$ Uptake Experiments. Cerebellar granule cells were plated in poly-L-lysine coated 96 well plates at a seeding density of $1 \times 10^6$ cells per ml (100 μl per well). Prior to experimental determination of $^{45}Ca^{2+}$ uptake, cells were exposed for 24 hours either to cytoprotective compound (10 μM) or vehicle control in incubation medium; some data were generated following 24 hr exposure to compounds (1 μM) in serum-free incubation medium. Cerebellar granule cells were washed twice with incubation medium supplemented with 15 mM glucose and 1.2 mM $MgCl_2$ prior to experiments and incubated in medium containing $^{45}Ca^{2+}$ (0.05 miCi/10 ml of experimental buffer). The cells were exposed to glutamate/glycine (100 μM/10 μM) in HBSS in the presence of $^{45}Ca^{2+}$. Cells were washed twice in incubation medium containing $MgCl_2$ to remove residual extracellular $^{45}Ca^{2+}$. The cells were then washed in $Ca^{2+}$-free KCl solution with digitonin (0.001%) for two minutes, to remove free cytosolic calcium from the cells. The digitonin-permeabilized cells were then lysed with 2% Triton®X-100 and radioactivity counted in a Beckman LS6500 Multi-Purpose Scintillation Counter. Each set of conditions was carried out in triplicate and repeated on at least three separate occasions. Essentially the same procedures were employed for cultured cortical neuron cells.

$^{45}Ca^{2+}$ uptake by cerebellar granule cells in response to glutamate was inhibited in cells that had been pretreated with compounds of the invention in the absence or presence of serum, relative to vehicle controls. $^{45}Ca^{2+}$ uptake by cortical neurons in response to glutamate was also inhibited in cells that had been pretreated with compounds of the invention, relative to controls. Accordingly, by decreasing intracellular $Ca^{2+}$ accumulations, the compounds of the invention protected the cells from glutamate-induced excitotoxicity that would otherwise have proceeded via apoptotic and/or necrotic mechanisms as sequelae to elevated levels of cytosolic $Ca^{2+}$.

Assay of Glutamate Toxicity by Lactate Dehydrogenase (LDH) Release. Cerebellar granule cells were plated ($1 \times 10^5$ cells per well) in 96 well plates (Becton-Dickinson black poly-d-lysine coated plates, BD Biosciences, San Jose, Calif.). Cells were pre-incubated with test cytoprotective compounds in the growth medium for 24 or 48 hr. The culture medium was aspirated and cells were exposed to 100 μM glutamate and 10 μM glycine in a HEPES-buffered salt solution (HBSS) containing 137 mM NaCl, 5 mM KCl, 10 mM $NaHCO_3$, 20 mM HEPES, 5.5 mM glucose, 0.6 mM $KH_2PO_4$, 1.4 mM $CaCl_2$, 0.9 mM $MgSO_4$. The NMDA receptor antagonist MK-801 (dizocilpine, Sigma, St. Louis, Mo.; 10 μM) was added to block NMDA receptor activation after 1 hour. Neuronal injury was assessed at 24 hours after the initial insult by quantitative measurement of Lactate Dehydrogenase (LDH) release using a cytotoxicity Detection Kit (Roche Molecular Biochemicals; Indianapolis, Ind.) according to the supplier's instructions.

LDH release by cerebellar granule cells in response to glutamate was inhibited in cells that had been pretreated with compounds of the invention, relative to vehicle controls. This observation reflected the cytoprotective effects of the invention compounds, insofar as decreased LDH release following the excitotoxic stimulus signified a decline in cell death among cells exposed to the compounds.

Example 6

Use of Compound No. 9 for Affinity Isolation of Excitotoxic Pathway Components

Immobilization of Compound No. 8 on NHS-activated beads to obtain Compound No. 9 is described above in Example 3. Glutamate-responsive cells comprising an excitotoxic pathway as described above (e.g., cerebellar granule cells or cortical neurons prepared as described in the preceding Example) are suspended in IB buffer (250 mM sucrose, 0.2 mM K+EGTA, 1 mM sodium succinate, 10 mM Tris, pH 7.8) or another suitable buffer depending on the characteristics of the component to be isolated, at a protein concentration of 25 mg/ml and stored at $-80°$ C. prior to use. To a 2 ml slurry of Compound No. 9 (i.e., Compound No. 8 immobilized on NHS-activated Sepharose™ beads) is added 2 ml of thawed cell lysate preparation and 5 ml of 2× column buffer (1% Triton X-100™, 2 M glycerol, 1 mM dithiothreitol, 1 mM $CaCl_2$, 40 mM sucrose, 1 mM TEA/EGTA and 25 mM TEA/TES, pH 7.3, supplemented with a standard protease inhibitor cocktail). The volume is brought to 10 ml by the addition of distilled water and the mixture is incubated for three hours at 4° C. with gentle agitation. The beads are pelleted by centrifugation and the supernatant is saved as the column-passed material fraction. The beads are washed twice with 2× column buffer and then packed into a disposable 10 ml column which is washed sequentially with 30 ml of 2× column buffer, 50 ml of 2× column buffer modified to contain 100 mM TEA/TES, 10 ml of the 100 mM TEA/TES buffer containing 10 mM TPP, and 50 ml of 2× column buffer containing 1 M NaCl. The column is then eluted by resuspending the beads in 10 ml of a solution containing 10 mM Cpd 8/40% (v/v) PEG 400/10% (v/v) EtOH eluate and 50% (v/v) 2× column buffer, removing the suspension to a tube and incubating the beads with gentle agitation for one hour at 4° C. The beads are pelleted and the supernatant saved; this elution step is then repeated. The collected column wash and elution fractions are standardized for protein content and electrophoresed on a 4-12% polyacrylamide-SDS NU-PAGE™ Tris-glycine gel using a MES buffering system (Invitrogen, Inc., Carlsbad, Calif.) according to the supplier's instructions. The gel is stained with SeeBlue Plus2™ (Invitrogen) to visualize affinity-isolated proteins.

Example 7

Cytoprotection in a Murine Retinal Explant Model for Retinitis Pigmentosa

This Example describes demonstration of cytoprotective activity of a compound synthesized according to Examples 1 and 2 above in a retinal explant organotypical culture system.

Retinas were dissected at postnatal day 7 from rd1 mutant mice (Bowes et al., 1990 *Nature* 347:677; Frasson et al., 1999 *Nat. Med.* 5:1183), which carry a spontaneous cGMP phosphodiesterase mutation in retinal rod photoreceptors, leading to rapid and premature rod cell apoptosis in this animal model for the ophthalmic degenerative disease retinitis pigmentosa (RP); control retinas were from the background strain (C3H). Retinas were mounted flat on nitrocellulose membranes attached to culture dish inserts and maintained in serum-free $R_{16}$ culture medium for 21 days, reflecting a stage corresponding to postnatal day 28 (Caffe et al., 2001 *J. Chem. Neuroanat.* 22:263).

To reduce interanimal variation, retinas from an individual animal were experimentally paired, with one retina being exposed to a test compound and the contralateral control given only the solvent vehicle. Hence, at the initiation of cultures, one retina of each pair was exposed to 1 µM of compound no. 5 (see Ex. 2, supra), and its paired contralateral control retina received an equivalent volume of the test compound vehicle (DMSO). Medium was changed every second day, and at day 21 of culture the preparations were fixed in buffered 4% paraformaldehyde and subsequently cut on a cryotome in 8 µm sections and stained with hematoxylin.

Slides containing the sections were coded and scored using light microscopy, by counting the rows of photoreceptors in the outer nuclear layer of the retina for five fields from each section. The five field values were averaged for each slide. Typically, six sections from each preparation were scored, representing different cutting depths, and the collected averages from the six slides were averaged to yield an average value of remaining rows of retinal photoceptors per retina, which value was used for statistical analysis. Data were analyzed by Student's paired t-test; ratios were also calculated of treated:untreated retinas from each intra-animal pair and analyzed by Student's one-group t-test, with the population mean set to 1.0. Data from one such experiment are set forth in Table 1, and are consistent with protection to a significantly greater extent of the retinal cells in the treated retinas relative to the untreated retinas.

TABLE 1

Murine rd1 Photoreceptor Cytoprotection in vitro

| Treatment (n) | No. Rows Photoreceptors | Paired t-test | Treated:Untreated | 1-group t-test |
|---|---|---|---|---|
| 1 µM Cpd no. 5 (4) | 2.11 ± 0.13 | p = 0.038 | 1.10 ± 0.10 | p = 0.144 |
| Control (4) | 1.87 ± 0.11 | | | |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the structure:

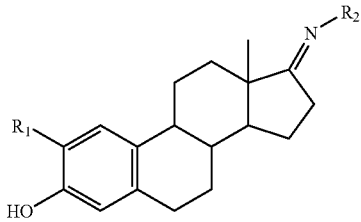

or a stereoisomer, prodrug or pharmaceutically acceptable salt thereof, wherein:

$R_1$ is adamantyl;

$R_2$ is —$NR_{3a}R_{3b}$, —O—$R_{3a}$, or —$NR_{3a}C(=O)R_{3b}$; and $R_{3a}$ and $R_{3b}$ are the same or different and independently selected from hydrogen, alkyl, substituted alkyl, aryl, substituted aryl, arylalkyl, substituted arylalkyl, heterocycle and substituted heterocycle.

2. The compound of claim 1, wherein $R_2$ is —$NR_{3a}R_{3b}$.

3. The compound of claim 2 wherein $R_{3a}$ and $R_{3b}$ are both hydrogen.

4. The compound of claim 1, wherein $R_2$ is —O—$R_{3a}$.

5. The compound of claim 4, wherein $R_{3a}$ is hydrogen.

6. The compound of claim 4 wherein $R_{3a}$ is lower alkyl.

7. The compound of claim 6, wherein $R_{3a}$ is methyl.

8. The compound of claim 1, wherein $R_2$ is —$NR_{3a}C(=O)R_{3b}$.

9. The compound of claim 8, wherein $R_{3a}$ is hydrogen and $R_{3b}$ is lower alkyl.

10. The compound of claim 9, wherein $R_{3b}$ is methyl.

11. A pharmaceutical composition comprising a compound of claim 1 in combination with a pharmaceutically acceptable carrier.

* * * * *

UNITED STATES PATENT AND TRADEMARK OFFICE
CERTIFICATE OF CORRECTION

PATENT NO. : 7,304,171 B2 Page 1 of 1
APPLICATION NO. : 11/138105
DATED : December 4, 2007
INVENTOR(S) : Pei It is certified that error appears in the above-identified patent and that said Letters Patent is hereby corrected as shown below:

On Title page Item [56]

Page 2, line 53, "OTHER PUBLICATIONS" the Deshpande, S., reference:

"Protective Role of Estrogen in the Neurodegenerative Disorder," should read

--Protective Role of Estrogen in the Neurodegenerative Disorders,--

Page 2, line 58, "OTHER PUBLICATIONS" reference "Du, D-M., et al" should read

--Du, D-M., et al.,--

Page 2, line 39, "OTHER PUBLICATIONS" reference Rapala, R., et al. "The

Adamantly Group in Medicinal Agents. II. Anabolic Steroid 17γ-Adamantoates,"

should read --The Adamantly Group in Medicinal Agents. II. Anabolic Steroid

17β-Adamantoates,--

Signed and Sealed this

Fifteenth Day of July, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,304,171 B2 |
| APPLICATION NO. | : 11/138105 |
| DATED | : December 4, 2007 |
| INVENTOR(S) | : Pei |

It is certified that error appears in the above-identified patent and that said Letters Patent is hereby corrected as shown below:

Title Page, Item (56)
Page 2
"OTHER PUBLICATIONS" reference Rapala, R., et al. "The Adamantly Group in Medicinal Agents. II. Anabolic Steroid 17γ-Adamantoates," should read -- The Adamantyl Group in Medicinal Agents. II. Anabolic Steroid 17β-Adamantoates, --

Signed and Sealed this

Second Day of September, 2008

JON W. DUDAS
*Director of the United States Patent and Trademark Office*